(12) United States Patent
Huntoon

(10) Patent No.: US 9,554,830 B2
(45) Date of Patent: Jan. 31, 2017

(54) DELIVERING DRUGS TO DESIRED LOCATIONS WITHIN A MAMMAL

(75) Inventor: Marc A. Huntoon, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 1147 days.

(21) Appl. No.: 13/580,870

(22) PCT Filed: Feb. 24, 2011

(86) PCT No.: PCT/US2011/026040
§ 371 (c)(1),
(2), (4) Date: Aug. 23, 2012

(87) PCT Pub. No.: WO2011/106502
PCT Pub. Date: Sep. 1, 2011

(65) Prior Publication Data
US 2012/0323219 A1  Dec. 20, 2012

Related U.S. Application Data

(60) Provisional application No. 61/308,158, filed on Feb. 25, 2010, provisional application No. 61/385,893, filed on Sep. 23, 2010.

(51) Int. Cl.
*A61B 17/70* (2006.01)
*A61M 25/09* (2006.01)
*A61M 37/00* (2006.01)
*A61M 39/02* (2006.01)

(52) U.S. Cl.
CPC .......... *A61B 17/7061* (2013.01); *A61M 25/09* (2013.01); *A61M 37/00* (2013.01); *A61M 37/0069* (2013.01); *A61M 39/0247* (2013.01); *A61M 2025/09125* (2013.01); *A61M 2025/09183* (2013.01); *A61M 2039/0261* (2013.01)

(58) Field of Classification Search
CPC ............ A61K 9/0024; A61M 37/0069; A61M 39/0247; A61M 37/00; A61M 25/09; A61M 2025/09125; A61B 17/3468; A61B 17/7061
See application file for complete search history.

(56) References Cited

U.S. PATENT DOCUMENTS 5,980,548 A * 11/1999 Evans ................... A61F 2/82
606/185
6,061,596 A   5/2000 Richmond et al.
6,181,965 B1  1/2001 Loeb et al.
(Continued)

FOREIGN PATENT DOCUMENTS

WO      WO9729802 A2   8/1997

OTHER PUBLICATIONS

Sheridan et al., "Bioabsorbable polymer scaffolds for tissue engineering capable of sustained growth factor delivery," Journal of Controlled Release, 64(1-3), Feb. 2000, pp. 91-102.
(Continued)

*Primary Examiner* — Bradley Osinski
(74) *Attorney, Agent, or Firm* — Fish & Richardson P.C.

(57) ABSTRACT

This document provides materials and methods related to delivering drugs to desired locations within a mammal. For example, materials and methods for implanting a guide wire and a drug eluting implant into a mammal are provided.

18 Claims, 25 Drawing Sheets

(56) References Cited

U.S. PATENT DOCUMENTS

| | | | |
|---|---|---|---|
| 6,949,117 B2 * | 9/2005 | Gambale | A61F 2/06 604/60 |
| 2003/0225418 A1 * | 12/2003 | Esksuri | A61F 2/013 606/108 |
| 2004/0010231 A1 | 1/2004 | Leonhardt et al. | |
| 2006/0178700 A1 | 8/2006 | Quinn | |
| 2007/0016163 A1 | 1/2007 | Santini, Jr. et al. | |
| 2007/0243225 A1 | 10/2007 | McKay | |
| 2007/0243228 A1 | 10/2007 | McKay | |
| 2008/0058876 A1 | 3/2008 | Barolat | |
| 2009/0112177 A1 | 4/2009 | Zanella | |
| 2009/0131908 A1 | 5/2009 | McKay | |
| 2009/0263448 A1 | 10/2009 | Hobot et al. | |
| 2009/0263460 A1 | 10/2009 | McDonald | |
| 2010/0015196 A1 | 1/2010 | Kimble et al. | |
| 2010/0112034 A1 | 5/2010 | McKay | |

OTHER PUBLICATIONS

Sokolsky-Papkov et al., "Polymer carriers for drug delivery in tissue engineering," Advanced Drug Delivery Reviews, 59(4-5), May 2007, pp. 187-206.

Burgher et al., "Transforaminal Epidural Clonidine versus Corticosteroid for Acute Lumbosacral Radiculopathy due to Intervertebral Disk Herniation," Spine, 36(5), Mar. 2011, pp. E293-E300.

* cited by examiner

DELIVERING DRUGS TO DESIRED LOCATIONS WITHIN A MAMMAL

CROSS-REFERENCE TO RELATED APPLICATIONS

This application is a National Stage application under 35 U.S.C. 371 of International Application No. PCT/US2011/026040, having an International Filing Date of Feb. 24, 2011, which claims the benefit of U.S. Provisional Application Ser. No. 61/385,893, filed Sep. 23, 2010, and U.S. Provisional Application Ser. No. 61/308,158, filed on Feb. 25, 2010. The disclosures of the prior applications are considered part of (and are incorporated by reference in) the disclosure of this application.

BACKGROUND

1. Technical Field

This document relates to materials and methods for delivering drugs to desired locations within a mammal. For example, this document provides materials and methods for implanting a guide wire and a drug eluting implant into a mammal.

2. Background Information

Current treatments for sciatica, for example, can include physical therapy, non-steroidal anti-inflammatory drug therapies, injections of corticosteroids via the epidural route, and surgical discectomies. Surgical discectomy can be expensive, and some patients can experience complications. A small percentage of patients can develop post-surgical pain, which can be exceedingly difficult to treat.

SUMMARY

This document relates to materials and methods for delivering drugs to desired locations within a mammal. For example, this document provides materials and methods for implanting a guide wire and one or more drug eluting implants into a mammal. In some cases, the guide wire can be implanted into a mammal under conditions wherein one end of the guide wire is fixed to a tissue (e.g., bone or muscle tissue) and the other end of the guide wire is positioned near the surface of the mammal's skin. In such cases, one or more drug eluting implants (e.g., drug eluting depots or pods) can be advanced over the guide wire to a desired location and allowed to elute a desired drug or degrade or become absorbed. Once the initial drug eluting implants exhibit reduced effectiveness or are degraded or absorbed, the free end of the guide wire located near the surface of the mammal's skin can be located and exposed, and one or more replacement drug eluting implants can be advanced over the guide wire to a desired location. The methods and materials provided herein can allow clinicians to administer drug eluting implants to the same location in a convenient and reproducible manner.

In general, one aspect of this document features a percutaneous drug delivery system for delivering multiple drug eluting implants to a mammal over time. The system comprises, or consists essentially of, a guide wire having a proximal end and a distal end, a tissue anchor attached to the distal end of the guide wire, and a pusher, wherein the pusher is configured to slide over the guide wire in a manner that is capable of advancing a drug eluting implant from the proximal end of the guide wire toward the distal end of the guide wire, wherein the guide wire is configured to have a length such that the distal end of the guide wire is located near a site to be treated within the mammal and the proximal end of the guide wire is located adjacent to the surface of the skin of the mammal. The mammal can be a human. The guide wire can be constructed of nitinol. The tissue anchor can be releasably attached to the distal end of the guide wire. The tissue anchor can be integral with the distal end of the guide wire. The guide wire can be configured to have a length such that the distal end of the guide wire is located within 1 cm of the site to be treated and the proximal end of the guide wire is located within 1 cm of the surface of the skin of the mammal. The system can comprise at least one drug eluting implant. At least one drug eluting implant can be a clonidine eluting implant. The tissue anchor can be a bone anchor. The tissue anchor can be a threaded bone anchor. The system can comprise a catheter comprising a distal end and a proximal end, and the catheter can be configured to house at least a portion of the guide wire and to be movable over the proximal end of the guide wire.

In another aspect, this document features a percutaneous drug delivery system for delivering multiple drug eluting implants to a mammal over time. The system comprises, or consists essentially of a guide wire having a proximal end and a distal end, a tissue anchor attached to the distal end of the guide wire, a catheter comprising a distal end and a proximal end, and a pusher, wherein the catheter is configured to house at least a portion of the guide wire and to be movable over the proximal end of the guide wire, wherein the pusher is configured to slide over the guide wire and within the catheter in a manner that is capable of advancing a drug eluting implant within the catheter from the proximal end of the guide wire toward the distal end of the guide wire, wherein the guide wire is configured to have a length such that the distal end of the guide wire is located near a site to be treated within the mammal and the proximal end of the guide wire is located adjacent the surface of the skin of the mammal.

In another aspect, this document features a method for percutaneously delivering a drug to a mammal. The method comprises, or consists essentially of (a) advancing a guide wire having a distal end and a proximal end into a position within the mammal such that the distal end of the guide wire is located at or near a site to be treated, wherein the distal end of the guide wire comprises a tissue anchor device, (b) attaching the tissue anchor device to a tissue located at or near the site, (c) positioning a drug eluting implant along the guide wire at a position located at or near the site, (d) positioning the proximal end of the guide wire at or near the surface of the skin of the mammal, and (e) leaving the guide wire in the position for at least five days. The mammal can be a human. The guide wire can be constructed of nitinol. The tissue anchor can be releasably attached to the distal end of the guide wire. The tissue anchor can be integral with the distal end of the guide wire. The guide wire can be configured to have a length such that the distal end of the guide wire is located within 1 cm of the site to be treated and the proximal end of the guide wire is located within 1 cm of the surface of the skin of the mammal. The drug eluting implant can be a clonidine eluting implant. The drug eluting implant can be bioabsorbable. The tissue anchor can be a bone anchor. The tissue anchor can be a threaded bone anchor. The guide wire can be left in the position for at least ten days. The guide wire can be left in the position for at least thirty days. The guide wire can be left in the position for at least sixty days. The drug eluting implant can be attached to the guide wire prior to the advancing step (a), and the positioning step (c) can be accomplished via the movement of the guide wire during the advancing step (a) and/or the attaching step (b). The method can further comprise, after at least five days: (i) exposing the proximal end of the guide wire, (ii) advancing a drug eluting implant along the guide wire to a position located at or near the site, and (iii) leaving the guide wire in the position at or near the surface of the skin of the mammal for at least five additional days.

In another aspect, this document features a bioport comprising, or consisting essentially of, a body portion defining an inner compartment and an anchor configured to attach the bioport to a target tissue within a mammal, wherein the body portion defines an opening configured to allow material to be inserted into the inner compartment when the bioport is located within the mammal. The material can be a drug or therapeutic agent. The inner compartment can comprise the material. The body portion can be attached to a wire-like structure defining a lumen. The wire-like structure can be configured such that material is capable of being advance from one end of the wire-like structure through the lumen to the inner compartment. The bioport can comprise a spooling device. The bioport can be an expandable bioport.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
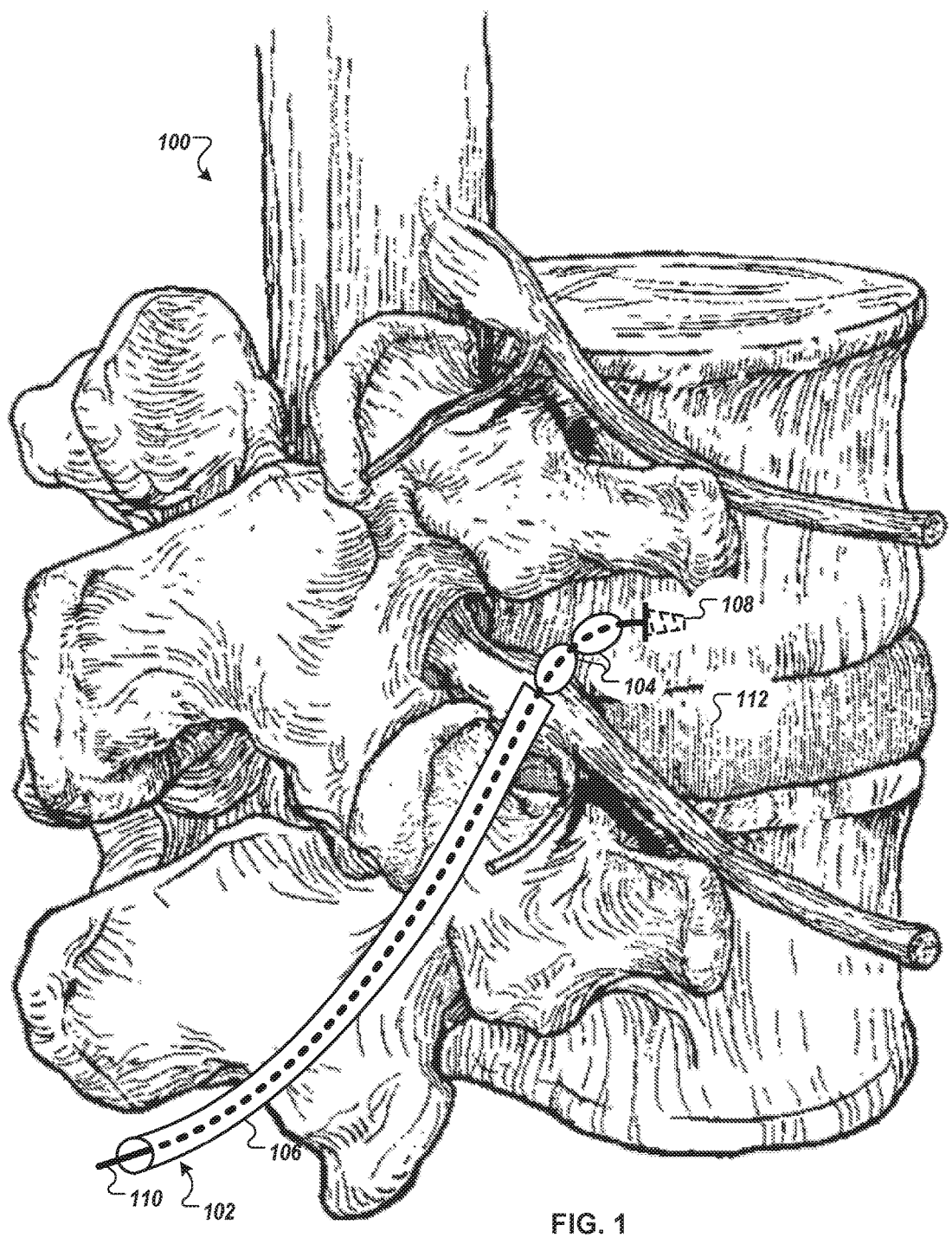
FIG. 1 is a perspective view of a portion of a spinal column and an example of a device for delivering a drug eluting implant (e.g., pod).

This document provides materials and methods for delivering drugs to desired locations within a mammal. For example, this document provides materials and methods for implanting a guide wire and one or more drug eluting implants into a mammal. The methods and materials provided herein can be used to deliver drugs to any desired location including, without limitation, nerves, wounds, tumor resection sites, intervertebral disks, bones, and visceral organs. In some cases, the methods and materials provided herein can be used to deliver drugs to tissue around the spine to treat pain (e.g., pain associated with sciatica or facet joint pain).

Any type of drug can be delivered using the methods and materials provided herein. Examples of such drugs include, without limitation, pain mediations such as clonidine, dexmedetomidine, opioids (e.g., morphine, hydromorphone, and fentanyl), bupivacaine, lidocaine, and ropivacaine to treat or reduce pain, anti-inflammatory drugs such as corticosteroids, acetaminophen, and etanercept to treat or reduce inflammation, anti-cancer drugs such as VEGF or angiogenesis inhibitors, cis-platin, and paclitaxel to treat or reduce cancer, and nucleic acid-based agents to treat a medical condition. Additional examples of anti-inflammatory agents that can be delivered using the methods and materials provided herein include, without limitation, salicylates, diflunisal, indomethacin, ibuprofen, naproxen, tolmetin, ketorolac, diclofenac, ketoprofen, fenamates (mefenamic acid, meclofenamic acid), enolic acids (piroxicam, meloxicam), nabumetone, celecoxib, etodolac, nimesulide, apazone, gold, sulindac or tepoxalin, antioxidants, such as dithiocarbamate, and other compounds such as sulfasalazine [2-hydroxy-5-[-4-[C2-pyridinylamino)sulfonyl]azo]benzoic acid], steroids such as fluocinolone, cortisol, cortisone, hydrocortisone, fludrocortisone, prednisone, prednisolone, methylprednisolone, triamcinolone, betamethasone, dexamethasone, beclomethasone, fluticasone, and combinations thereof. Examples of anabolic growth or anti-catabolic growth factors that can be delivered using the methods and materials provided herein include, without limitation, nerve growth factor, bone morphogenetic proteins, growth differentiation factors, LIM mineralization proteins, CDMP, and combinations thereof. In some cases, one or more pain medications or analgesic agents including, without limitation, acetaminophen, lidocaine, bupivicaine, opioid analgesics (e.g., buprenorphine, butorphanol, dextromoramide, dezocine, dextropropoxyphene, diamorphine, fentanyl, alfentanil, sufentanil, hydrocodone, hydromorphone, ketobemidone, levomethadyl, meperidine, methadone, morphine, nalbuphine, opium, oxycodone, papavereturn, pentazocine, pethidine, phenoperidine, piritramide, dextropropoxyphene, remifentanil, tilidine, tramadol, codeine, dihydrocodeine, meptazinol, dezocine, eptazocine, and flupirtine), and combinations thereof can be delivered using the methods and materials provided herein. In some cases, an analgesic agent can include agents with analgesic properties such as, for example, amitriptyline, carbamazepine, gabapentin, pregabalin, clonidine, and combinations thereof. Additional examples of drugs that can be delivered as described herein include, without limitation, those described elsewhere (see, e.g., paragraphs [0061] to [0067] of U.S. Patent Application Publication No. 2009/0263460 and paragraphs [0021] to [0026] of U.S. Patent Application Publication No. 2007/0243228). In some cases, one or more anti-inflammatory agents, one or more analgesic agents, one or more osteoinductive growth factors, or combinations thereof can be delivered to a mammal as described herein.

The methods and materials provided herein can be used to treat any type of mammal including, without limitation, humans, monkeys, horses, cows, pigs, sheep, dogs, and cats. As described herein, a guide wire can be implanted into a desired location within a mammal, and one or more drug eluting implants can be advanced over the guide wire into position. In some cases, one end of the guide wire can be anchored to a tissue within the mammal (e.g., bone or muscle tissue), and one or more drug eluting implants can be passed along the guide wire to the treatment site. A guide wire can be anchored or fixed to any type of tissue including, without limitation, bone such as a lumbar vertebral body (e.g., L1, L2, L3, L4, or L5 vertebral bodies), a cervical vertebral body, a thoracic vertebral body, a pedicle, a transverse processes, or articulating processes, a sacrum or sacroiliac joint, a muscle such as psoas major, multifidi, and erector spinae, spinal discs such as L1-L2 discs, L2-L3 discs, L3-L4 discs, L4-L5 discs, and L5-S1 discs, tendons, or ligaments such as posterior longitudinal ligaments, mammillo-accessory ligaments, and interspinous ligaments. The other end of the guide wire can be positioned near the surface of the mammal's skin to allow easy access so that additional drug eluting implants can be positioned within the mammal at a later date. For example, the guide wire can remain in situ, thereby allowing additional drug eluting implants or other treatments to be passed along the guide wire to the same treatment site at a later date. In some cases, a spool can be used to house at least a portion of the excess guide wire. In such cases, the spool can be positioned near the surface of the mammal's skin to allow easy access so that additional drug eluting implants can be positioned within the mammal at a later date. For example, a spool having the proximal end of the guide wire can remain in situ, thereby allowing additional drug eluting implants or other treatments to be passed along the guide wire to the same treatment site at a later date.

FIG. 1 is a perspective view that shows a portion of a spinal column 100 and an example of a device 102 for delivering at least one drug eluting implant 104 to a treatment site within a patient. Device 102 can include a catheter 106 (or a needle), an anchor 108, and a guide wire 110. Anchor 108 can be inserted into a bone, such as a posterior aspect of a vertebral body near an exiting spinal nerve, to fix one end of device 102. Anchor 108 can be, for example, a bone screw, a nitinol corkscrew anchor, or other bone/tissue anchoring device. In some cases, anchor 108 can be left implanted in the patient with no need to remove it. Guide wire 110 can be connected to anchor 108 and threaded through catheter 106 and drug eluting implant 104 so that drug eluting implant 104 can be passed along guide wire 110 to the treatment site, such as near an exiting spinal nerve 112.

In some cases, device 102 can be inserted using fluoroscopy, magnetic resonance imaging (MRI), ultrasound (US), or computed tomography (CT) via a percutaneous needle (e.g., a 12- or 14-gauge needle). In some cases, drug eluting implant 104 and guide wire 110 can be preloaded in a needle. For example, a package containing device 102 or parts of device 102, such as drug eluting implant 104, guide wire 110, and/or anchor 108, can be preloaded for insertion into a patient. Drug eluting implant 104 can contain a pain and/or inflammation reliever. For example, drug eluting implant 104 can contain clonidine or other anticytokine drugs to relieve pain and inflammation associated with spinal nerve irritation.

Figure 12:
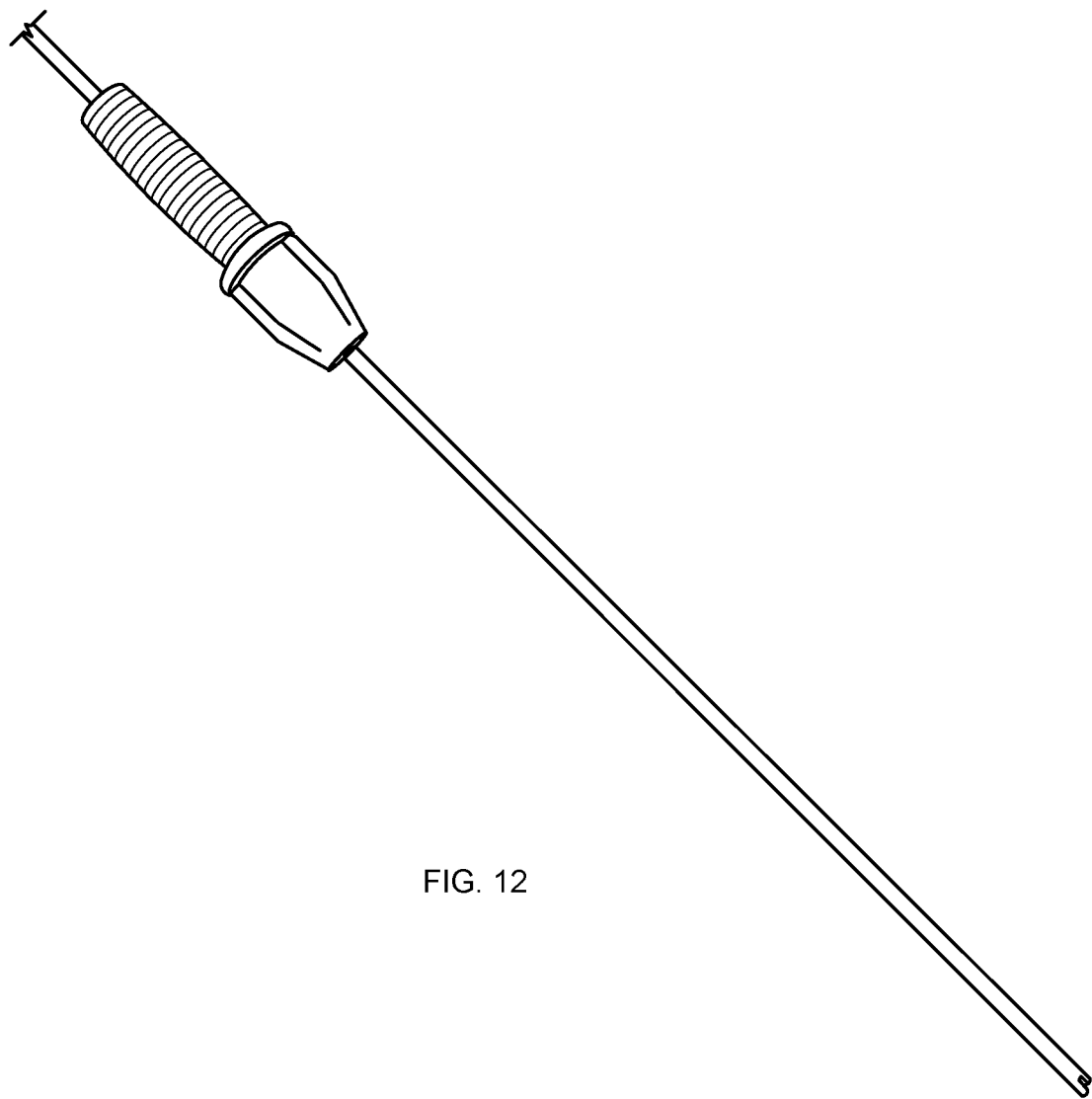
FIG. 12 is a photograph of an exemplary delivery catheter that can be used to deliver a drug eluting implant to a treatment site.
Figure 13:
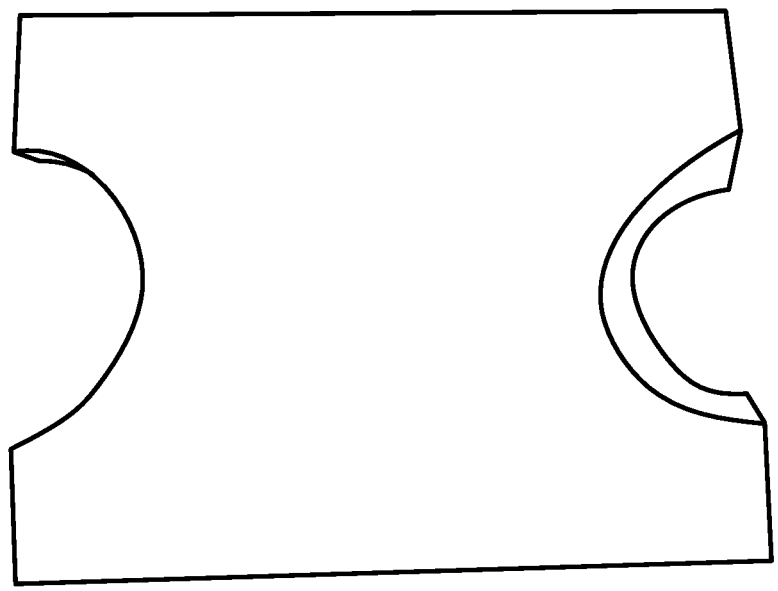
FIG. 13 is a photograph of an exemplary spooling device having indentations to hold excess wire in position.
Figure 14:
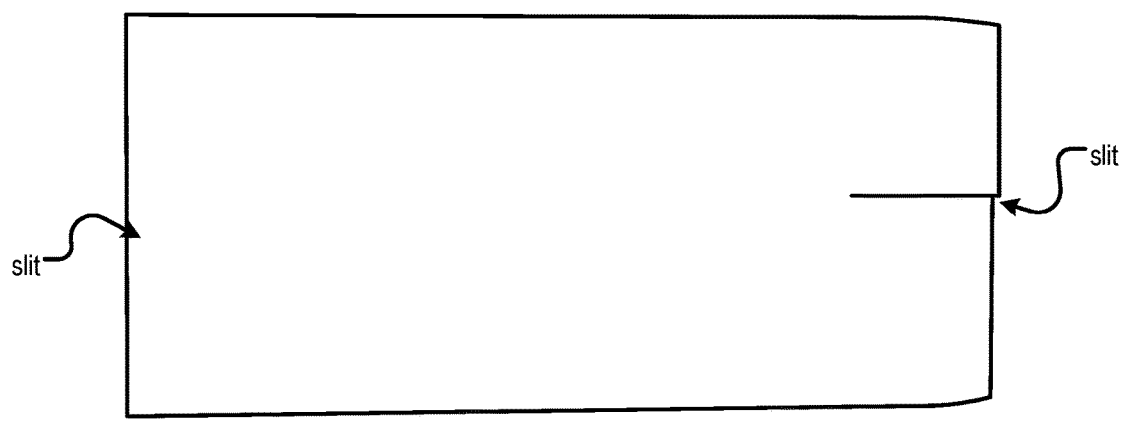
FIG. 14 is a photograph of an exemplary spooling device having slits to hold excess wire in position.
Figure 15:
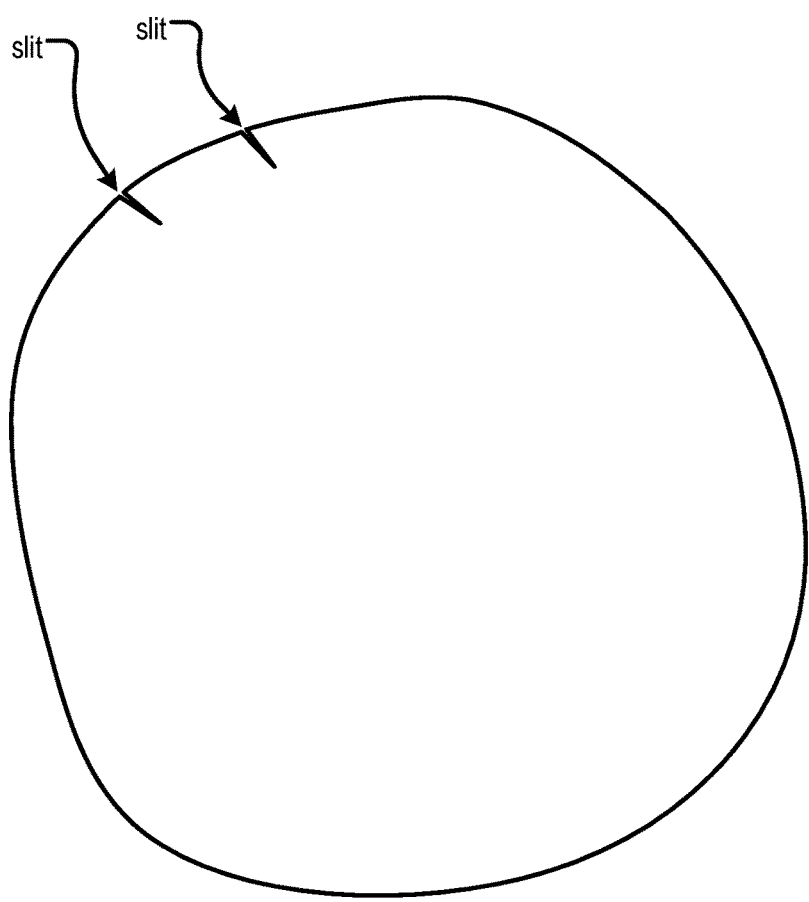
FIG. 15 is a photograph of an exemplary spooling device having slits to hold excess wire in position.
Figure 16:
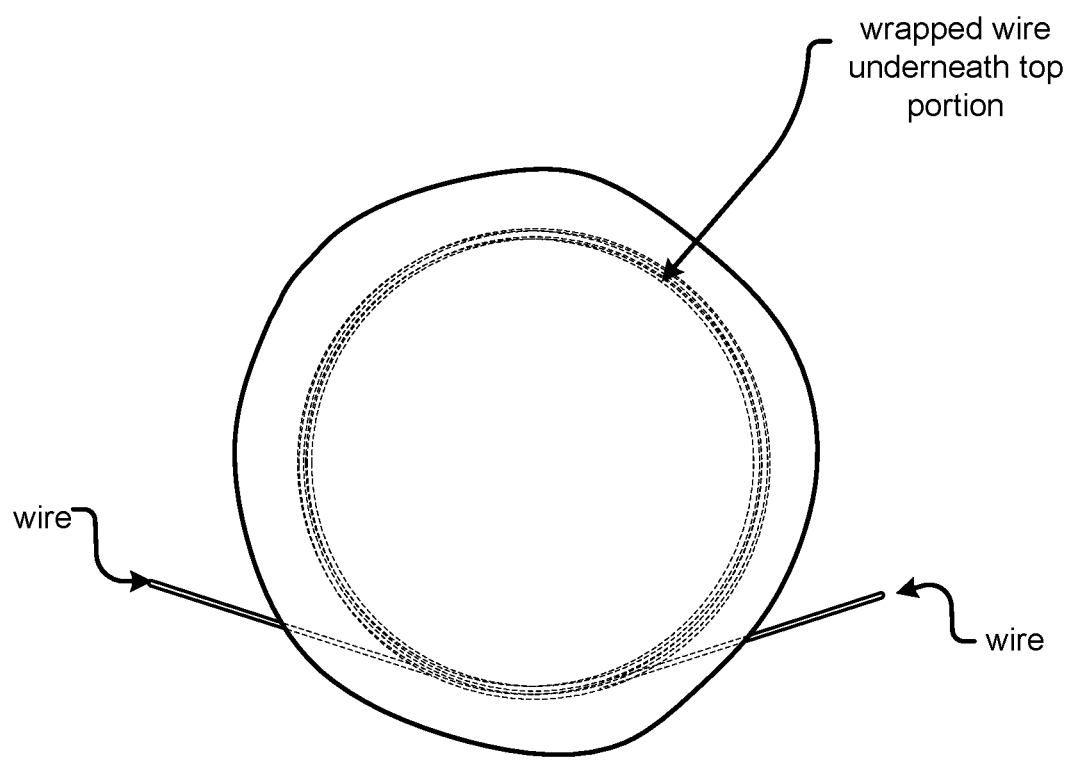
FIG. 16 is a photograph of a top view of an exemplary spooling device.
Figure 17:
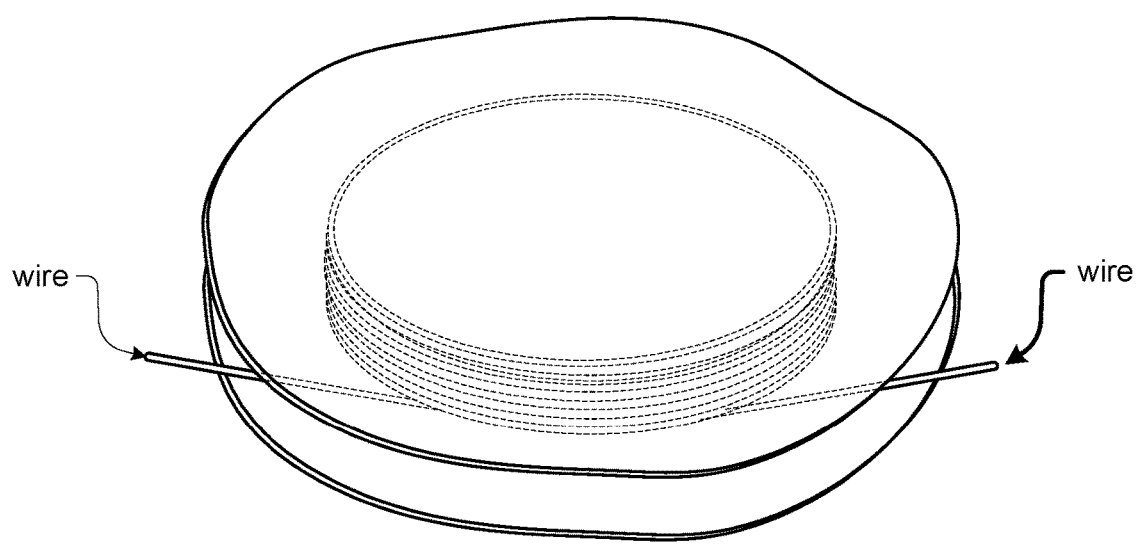
FIG. 17 is a photograph of partial side view of an exemplary spooling device.
Figure 18:
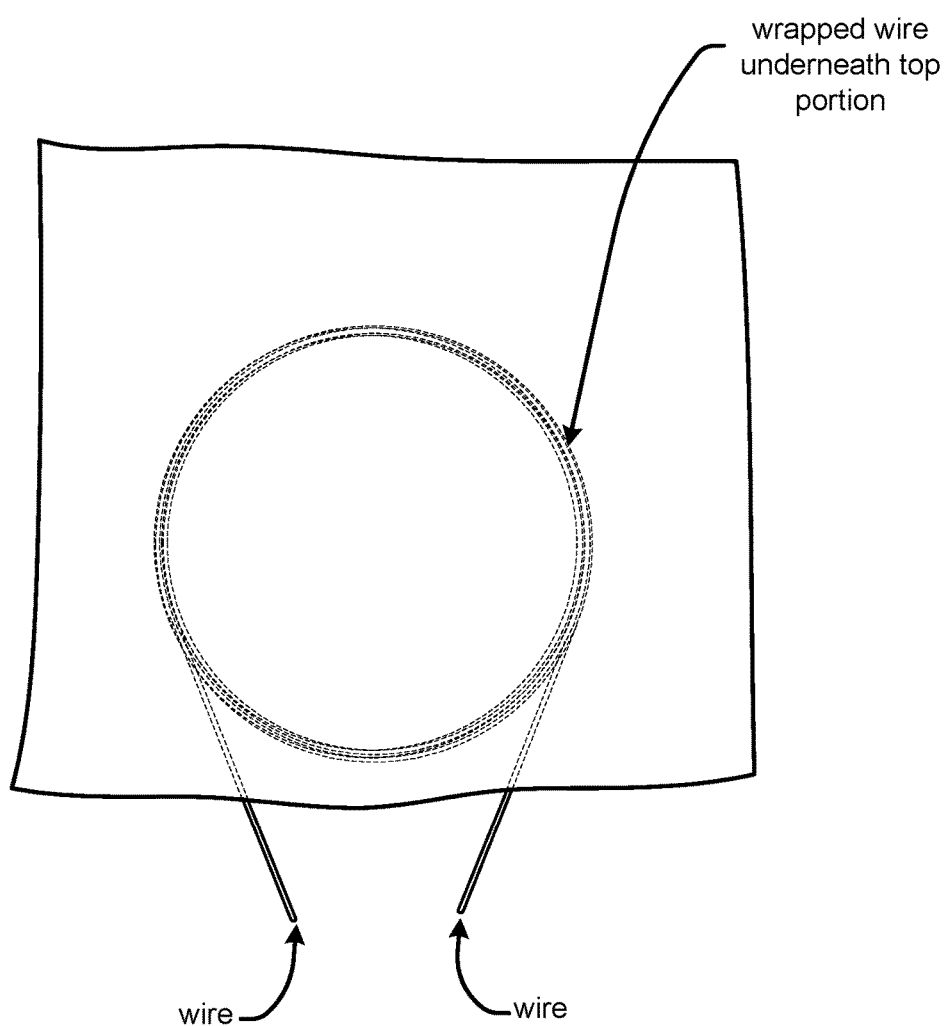
FIG. 18 is a photograph of a top view of an exemplary spooling device.
Figure 19:
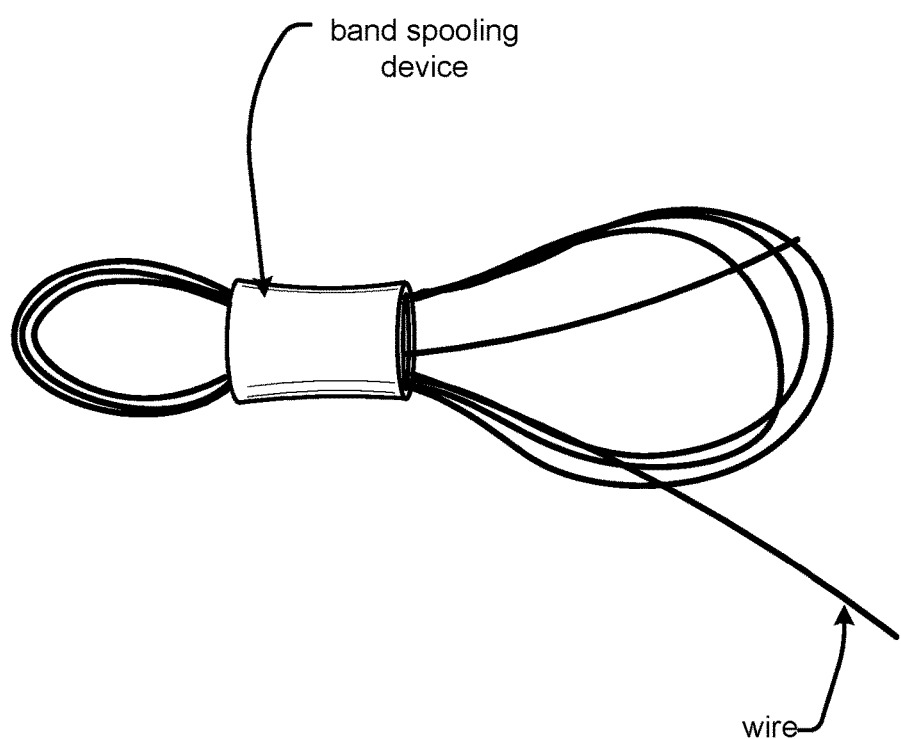
FIG. 19 is a photograph of a top view of an exemplary spooling device.
Figure 20:
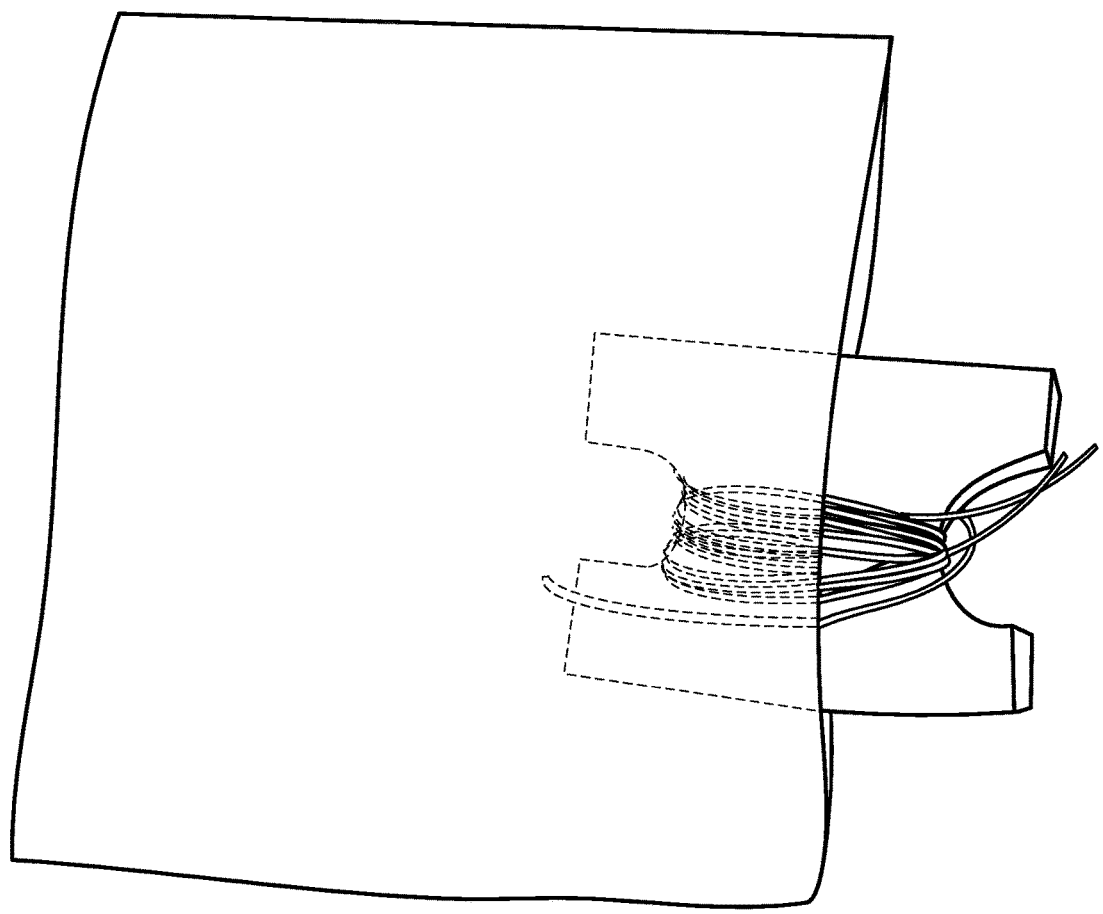
FIG. 20 is a photograph of the exemplary spooling device of FIG. 13 being tucked under a membrane designed to simulate skin.

In some cases, a device provided herein can be implanted by carrying out all or a subset of the following steps: (a) delivering a needle (e.g. a needle with a stylet in place to prevent a tissue plug) to a desired treatment site, (b) removing the stylet from the needle, (c) pre-drilling a pilot hole for an anchor, (d) inserting a delivery catheter pre-loaded with an anchor, a guide wire, and a first drug eluting implant, (e) using the delivery catheter to insert the anchor (e.g., screw in the anchor), (f) removing the delivery catheter from the patient while leaving the anchor, guide wire, and first drug eluting implant within the patient, and (g) tucking excess guide wire under the patient's skin using a spooling device. FIG. 12 contains one example of a delivery catheter that can be used to deliver a drug eluting implant to a treatment site.

In some cases, drug eluting implant 104 can have a cylindrical shape (e.g., a cylindrical shape that maximizes volume while still passing easily through catheter 106). In some cases, drug eluting implant 104 can have another shape, such as the spheroid shape shown in FIG. 1. In some cases, drug eluting implant 104 can be made of a slowly biodegradable matrix that can allow additional implants to be passed along guide wire 110 at a later time without the need to remove previously inserted implants. For example, a drug eluting implant can be configured to have an implant design as described elsewhere (see, e.g., U.S. Patent Application Publication No. 2007/0243228). In some cases, a drug eluting implant can be formulated as described elsewhere (see, e.g., U.S. Patent Application Publication Nos. 2009/0263448 and 2009/0263460).

Guide wire 110 can act as a rail for over the wire delivery of drug eluting implants (e.g., pellets or pods) or catheters. In some cases, guide wire 110 can be referred to as a stylet. In some cases, guide wire 110 can be made of a metal alloy (e.g., nitinol). Alternatively or in addition, guide wire 110 can be coated with one or more antimicrobial agents (e.g., chlorhexidine) or silver to prevent infection. In some cases, guide wire 110 can include reference markings (e.g., echogenic, visible under fluoroscopy, magnetic, or electronic) to indicate the distance and/or location of anchor 108 relative to the proximal end of guide wire 110, as an aid to implant and/or catheter delivery. For example, guide wire 110 and/or catheter 106 can include a piezoelectric crystal to enable forward or side-viewing ultrasound guidance. In another example, guide wire 110 and/or catheter 106 can include a light and camera for direct visualization. When drug delivery is no longer needed, the reference markings and/or imaging aids can be used to remove anchor 108 and guide wire 110.

Catheter 106 can protect drug eluting implant 104 and prevent drug eluting implant 104 from damage or obstruction as drug eluting implant 104 is advanced into position. Catheter 106 can be removed after drug eluting implant 104 is placed at the treatment site. Catheter 106 can then be reinserted prior to inserting another drug eluting implant. In some cases, catheter 106 can remain in situ with guide wire 110 between insertions of drug eluting implants.

In some cases, catheter 106 can include drug delivery ports and can be accessible from outside the patient. A drug delivery port can be anchored over the guide wire and attached to a drug reservoir/pump. In addition to peridiscal/perineural delivery of pain medication, catheter 106 (or drug eluting implant 104) can be used for other medical treatments, such as local delivery of chemotherapy to a tumor or tumor resection site.

In some cases, anchor 108 can include threads, such that when anchor 108 and/or device 102 are turned in a first direction (e.g., clockwise), anchor 108 is screwed into the bone. This allows device 102 to be temporarily attached to bone. In some cases, anchor 108 and/or device 102 can be turned in the opposite direction (e.g., counter-clockwise) some time later to remove anchor 108, such as when the treatment is complete. In the case of treatment of sciatica, anchor 108 can be set in the posterior aspect of the vertebral body. In some cases, anchor 108 can be set with one clockwise turn, and released at a later date by a counter-clockwise motion. In some cases, anchor 108 can be composed of biodegradable materials that may promote bone growth (e.g., polylactic acid, bone morphogenetic protein (BMP), hydroxyapatite, or a combination thereof) and can be left within the patient without being removed at a later date. Anchor 108 can be embedded in wax or housed in a sheath for delivery under fluoroscopic guidance. In some cases, anchor 108 (e.g., an anchor screw) can be formed from or impregnated with hydroxyapatite crystals or cadaver bone to form nascent bone or be internalized in the existing bone matrix.

In some cases, anchor 108, guide wire 110, and drug eluting implant 104 can remain in situ. The free end of guide wire 110 can remain subcutaneously near the entry site, for example, within the subcutaneous tissue of the back of the patient for later retrieval. For example, after about thirty to forty-five days in situ (e.g., in the case of clonidine treatment for sciatica), device 102 can be pictured via fluoroscopy and a small incision can be made to locate the superficial aspect of device 102 (e.g., the free end of guide wire 110 or a spool device). In a case where the guide wire is anchored to a spinal disc or bone, the intradiscal stylet screw or bone screw can be retracted via a counterclockwise action, and the entire stylet can be detached from the disc or bone and removed. The drug elution may be successful in management of the early phase of sciatica, and effectively reduce the need for operative discectomy.

Figure 2A:
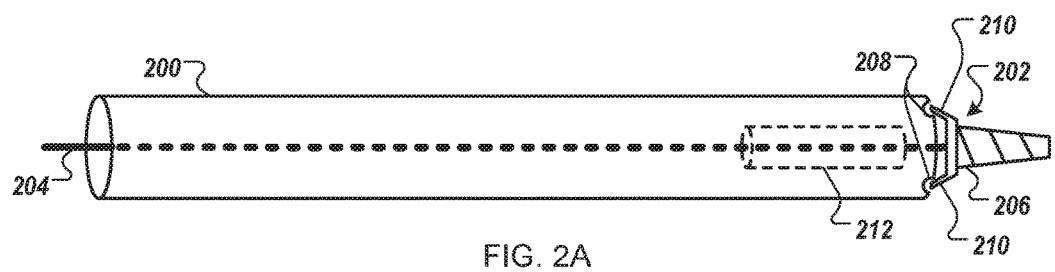
FIG. 2A is a cut away view of an example of a catheter for anchoring a drug eluting implant delivery device.

FIG. 2A is a cut away view that shows an example of a catheter 200 for anchoring a drug eluting implant delivery device 202. Drug eluting implant delivery device 202 can include a guide wire 204 (e.g., a nitinol stylet) that passes through catheter 200. The distal end of guide wire 204 can be connected to an anchor 206, and the distal end of catheter 200 can be removably connected to anchor 206.

Catheter 200 can include one or more structures 208 that engage with one or more structures 210 on anchor 206, so that turning catheter 200 while the structures are engaged with one another, results in turning anchor 206 as well. For example, catheter 200 can be turned clockwise to cause anchor 206 to grab or be inserted into a posterolateral disc annulus or spinal bone. In some cases, rotating catheter 200 in a first direction (e.g., clockwise) can cause structures 208 of catheter 200 to engage structures 210 of anchor 206. Conversely, rotating catheter 200 in the opposite direction (e.g., counter-clockwise) can cause structures 208 of catheter 200 to disengage structures 210 of anchor 206, thereby releasing anchor 206 from catheter 200 and leaving anchor 206, guide wire 204, and a drug eluting implant behind.

The distal end of guide wire 204, near anchor 206, can include a drug eluting implant 212. In some cases, drug eluting implant 212 can be attached to guide wire 204. In some cases, drug eluting implant 212 can slide along guide wire 204, such as either freely or under some friction requiring a particular amount of force to move drug eluting implant 212 along guide wire 204. For example, the amount of force may be more than what drug eluting 212 is typically exposed to when left in situ.

In some cases, the position of drug eluting implant 212 along guide wire 204 can be chosen so that the final location of drug eluting implant 212 within the patient is near the treatment site, such as near an exiting spinal nerve of interest or at the associated dorsal root ganglion. This may include measuring the distance between the insertion point of anchor 206 in a disc or spinal bone and the treatment site for the particular patient. Alternatively, an average or typical distance between an anchor insertion point and the treatment site can be used. In some cases, drug eluting implant 212 can be pre-positioned along guide wire 204 within catheter 200 prior to inserting catheter 200 into the patient.

In some cases, guide wire 204 can be freed from anchor 206 and drug eluting implant 212. In such cases, guide wire 204 and catheter 200 can then be removed. In the case of treatment of sciatica (e.g., radiculopathy) using clonidine, after a six week period of drug elution, anchor 206 can then be removed under fluoroscopic guidance via a percutaneous technique.

Figure 2B:
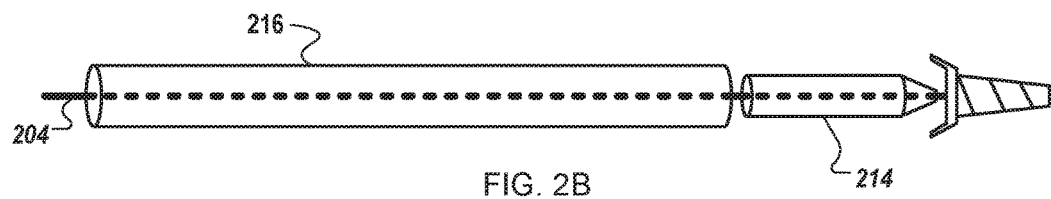
FIG. 2B is a cut away view of an example of a device for delivering a pointed drug eluting implant using a pusher.

FIG. 2B is a cut away view that shows an example of a device for delivering a pointed drug eluting implant 214 using a pusher 216. The pointed tip of drug eluting implant 214 can be integral to drug eluting implant 214 or a separate component. Where the pointed tip is a separate component, the pointed tip can be bioabsorbable and/or drug-eluting. Pusher 216 can be used to push drug eluting implant 214 along guide wire 204 to a treatment location within the patient. The pointed tip can aid in circumnavigating obstructions along the path to the treatment location.

Figure 2C:
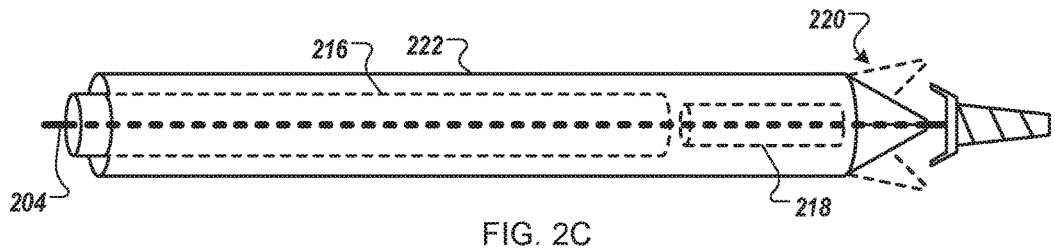
FIG. 2C is a cut away view of an example of a device for delivering a drug eluting implant through an actuating tip of a catheter.

FIG. 2C is a cut away view that shows an example of a device for delivering a drug eluting implant 218 through an actuating tip 220 of a catheter 222. After catheter 222 and/or drug eluting implant 218 have been passed over guide wire 204 to the target site, actuating tip 220 of catheter 222 can be opened via a hinge or other mechanism to release drug eluting implant 218. In addition, pusher 216 can be used to push drug eluting implant 218 beyond catheter 222, or catheter 222 can be pulled back in the hinge open configuration, leaving drug eluting pod 218 in place. Pusher 216 can include reference markings (e.g., visual markers) to aid in determining when the treatment site within the patient has been reached.

Figure 2D:
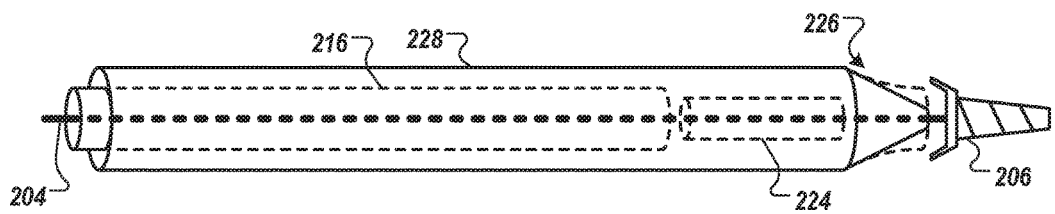
FIG. 2D is a cut away view of an example of a device for delivering a drug eluting implant through a membrane tip of a catheter.

FIG. 2D is a cut away view that shows an example of a device for delivering a drug eluting implant 224 through a membrane tip 226 of a catheter 228. After catheter 228 is advanced to reach the target site and/or is advanced over guide wire 204 to reach anchor 206 when guide wire 204 and anchor 206 are already in position, pusher 216 can be used to advance drug eluting pod implant 224 distally along guide wire 204, thereby pushing out a plug from membrane tip 226 or, in the case of a deformable membrane, expanding membrane tip 226 as drug eluting implant 224 is released from catheter 228.

Figure 4A:
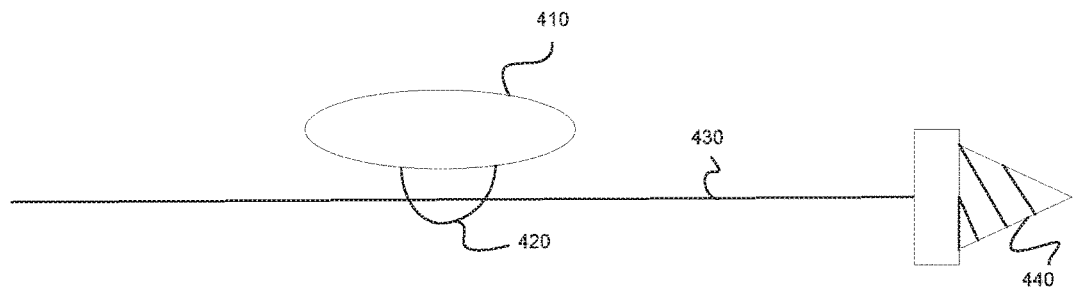
FIGS. 4A-B are side views of exemplary delivery systems.
Figure 4B:
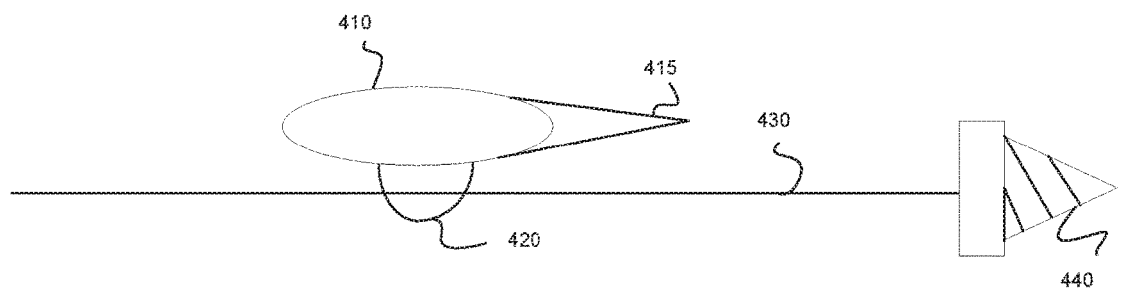

In some cases, a drug eluting implant provided herein can include a structure configured to allow the drug eluting implant to be advanced along a guide wire. For example, with reference to FIG. 4A, drug eluting implant 410 can include a structure 420. Structure 420 can be configured into any appropriate shape (e.g., a ring or loop) to allow drug eluting implant 410 to be advanced along guide wire 430 toward anchor 440. Structure 420 can be made of the same material as drug eluting implant 410 or a different material. In some cases, both drug eluting implant 410 and structure 420 are made from a bioabsorbable material (e.g., poly α-hydroxy acids such as poly(lactic acid) (PLA), poly (glycolic acid) (PGA), poly(lactide-co-glycolide) (PLGA) polymers, and polyhydroxyalkanoates (PHAs)). Other examples of bioabsorbable materials that can be used as described herein include, without limitation, those described elsewhere (Sheridan et al., *J. Controlled Release*, 64:91-102 (2000) and Sokolsky-Papkov et al., *Adv. Drug Delivery Rev.*, 59:187-206 (2007)). In some cases, a drug eluting implant provided herein can include a tip portion. With reference to FIG. 4B, a tip portion 415 can be configured to allow easier movement of drug eluting implant 410 along guide wire 430 toward anchor 440. Tip portion 415 can be made of the same material as drug eluting implant 410 or a different material. In some cases, both drug eluting implant 410 and tip portion 415 are made from a bioabsorbable material.

Figure 5A:
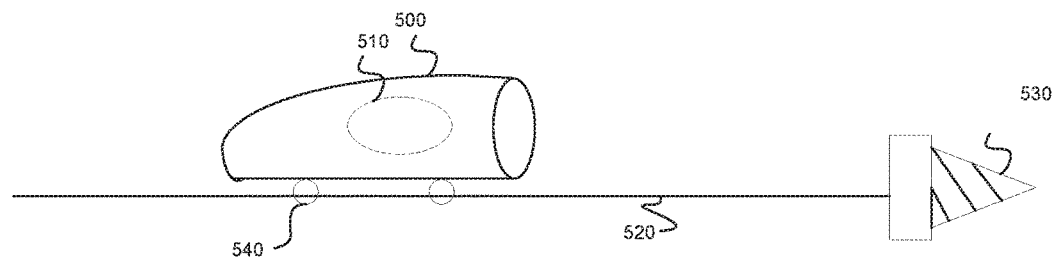
FIGS. 5A-F are side views of exemplary delivery systems having carriers.

In some cases, a carrier can be used to deliver one or more drug eluting implants provided herein into position. For example, with reference to FIG. 5A, carrier 500 can be configured to deliver drug eluting implant 510 along guide wire 520 toward anchor 530. Carrier 500 can be configured into any appropriate shape (e.g., oval shaped or funnel shaped) to allow drug eluting implant 510 to be entirely or at least partially housed within carrier 500 and to allow drug eluting implant 510 to be advanced along guide wire 520 toward anchor 530. In some cases, carrier 500 can include one or more structures 540. Structure 540 can be configured into any appropriate shape (e.g., a ring or loop) to allow carrier 500 to be advanced along guide wire 520 toward anchor 530. Structure 540 can be made of the same material as drug eluting implant 510 or a different material, or can be made of the same material as carrier 500 or a different material. In some cases, both carrier 500 and structure 540 are made from a non-bioabsorbable material. In other cases, both drug eluting implant 510 and structure 540 are made from a bioabsorbable material.

Figure 5B:
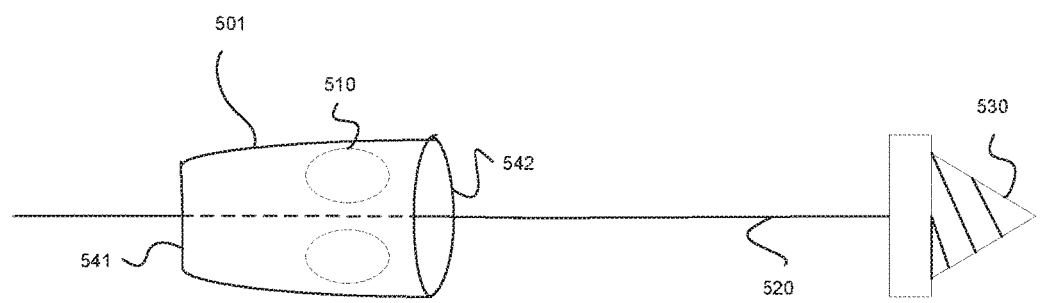
Figure 5C:
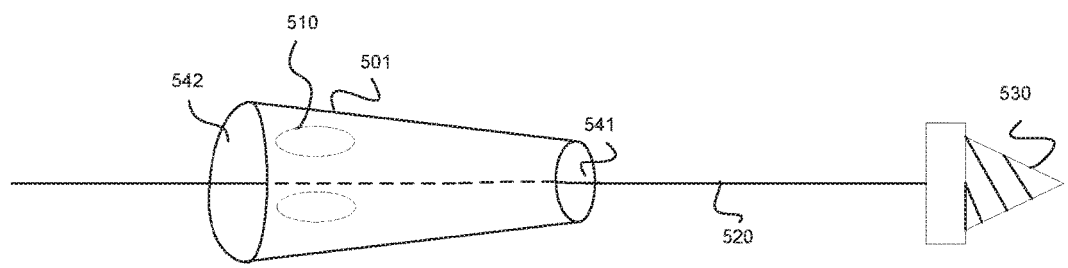

With reference to FIG. 5B, carrier 501 can be configured to entirely or at least partially house one or more drug eluting implants 510. Carrier 501 can be configured to deliver drug eluting implant 510 along guide wire 520 toward anchor 530. In some cases, carrier 501 can be configured to have a small open end 541 and a large open end 542. These opening ends can allow carrier 501 to be advanced along guide wire 520 toward anchor 530. In some cases, large open end 542 can be the leading end that advance toward anchor 530 (FIG. 5B). In other cases, small open end 541 can be the leading end that advance toward anchor 530 (FIG. 5C). In some cases, the opening ends can be the same size.

Figure 5D:
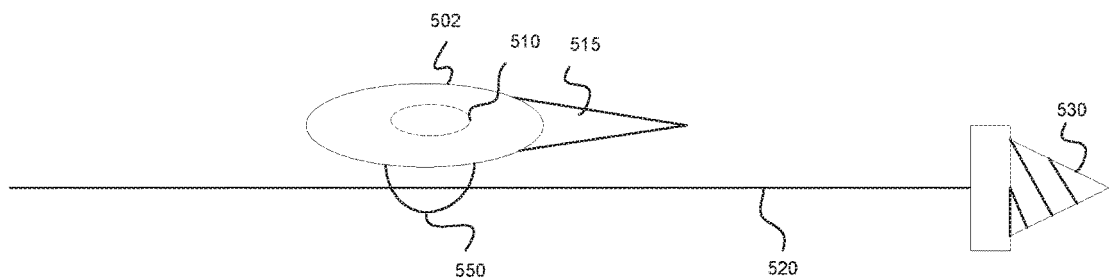

With reference to FIG. 5D, carrier 502 can be configured to enclose a drug eluting implant 510. In some cases, carrier 502 can include one or more structures 550. Structure 550 can be configured into any appropriate shape (e.g., a ring or loop) to allow carrier 502 to be advanced along guide wire 520 toward anchor 530. In some cases, carrier 502 can include a tip portion 515. Tip portion 515 can be configured to allow easier movement of carrier 502 along guide wire 520 toward anchor 530.

The carriers provided herein (e.g., carrier 500, carrier 501, or carrier 502) can be made of any appropriate material. For example, a carrier provided herein can be made of porous materials, mesh materials, biodegradable materials, bioabsorbable materials, or combinations thereof. In some cases, a carrier is made of a hard plastic material or other hard material such that the carrier can enable the drug eluting implant(s) to be transported safely to the treatment site.

Figure 6A:
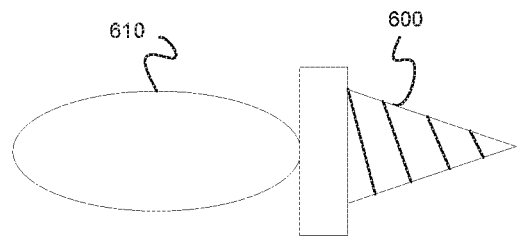
FIGS. 6A-F are side views of exemplary devices for delivering a drug to a treatment site.
Figure 6B:
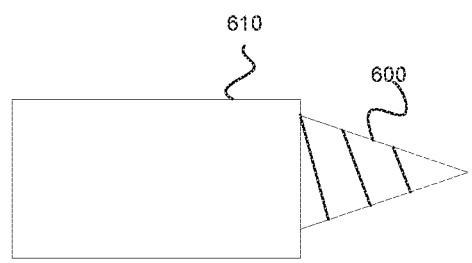
Figure 6C:
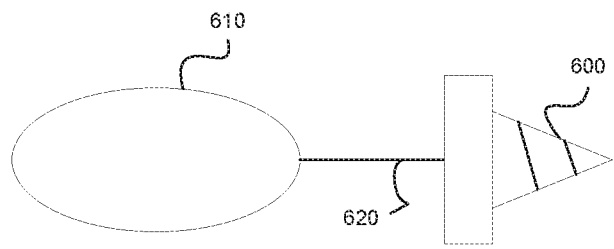
Figure 6D:
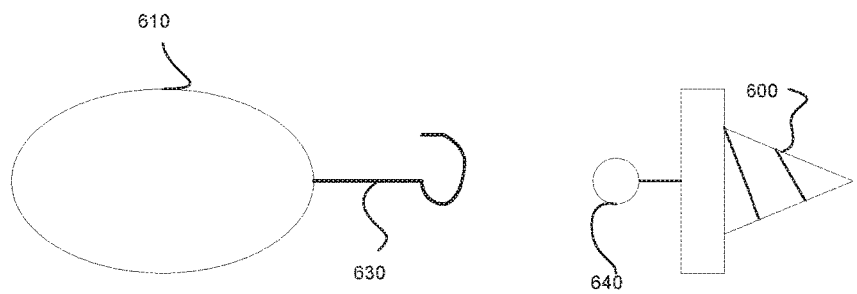
Figure 6E:
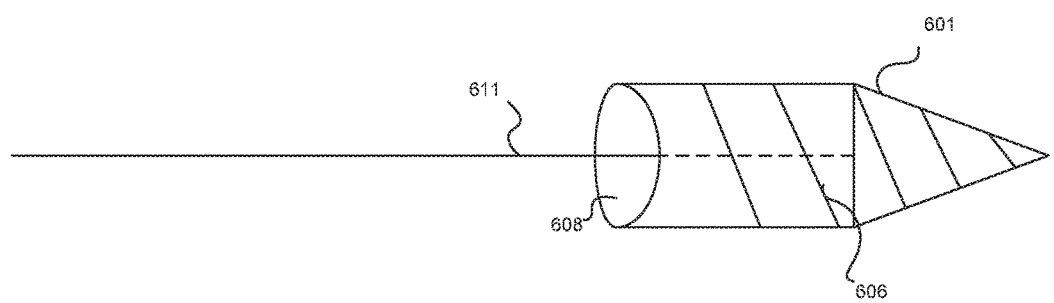

In some cases, a drug eluting implant provided herein can be integral with or attached to (e.g., releasably attached to) an anchor. With reference to FIG. 6A, drug eluting implant 610 can be directly attached to anchor 600. In some cases, drug eluting implant 610 can be integrally part of anchor 600 (FIG. 6B). For example, a screw-type anchor can be designed to have a screw portion and a drug eluting implant portion. In such cases, the screw portion can be made of a metal material (e.g., titanium), and the drug eluting implant portion can be made of a bioabsorbable material (e.g., PLG). In some cases, drug eluting implant 610 can be attached to anchor 600 via a tethering structure 620 (FIG. 6C). In some cases, drug eluting implant 610 can be releasably attached to anchor 600 via mating attachment structures such as a hook structure 630 and a loop structure 640 (FIG. 6D). In some cases, with reference to FIG. 6E, an anchor 601 can be configured to have threads 606 and a chamber 608. Anchor 601 can be attached to guide wire 611. Chamber 608 can be configured to allow a drug eluting implant to be entirely or at least partially housed within chamber 608. In some cases, replacement drug eluting implants can be positioned within chamber 608 by advancing a drug eluting implant along guide wire 611.

Figure 7A:
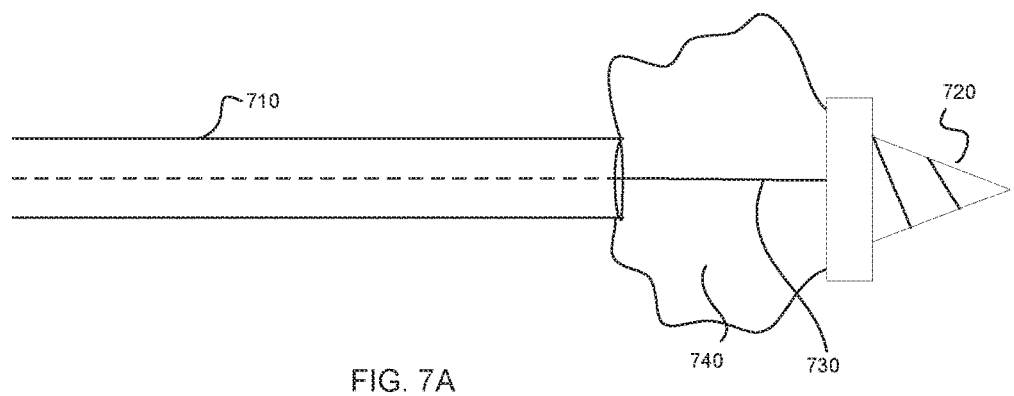
FIGS. 7A-D are side views of exemplary devices for delivering a drug to a treatment site.

This document also provides drug delivery devices. For example, with reference to FIG. 7A, drug delivery device 700 can include a catheter or tubular member 710, an anchor 720, and a guide wire 730. Catheter 710 can advance over guide wire 730 such that the distal end of catheter 710 is located near a site to be treated. Typically, the site to be treated is near the location where anchor 720 was attached to a particular tissue (e.g., a particular bone such as a transverse process when treating facet joint pain). Once catheter 710 is in position, a drug solution 740 (e.g., a drug/polymer combination designed to solidify in situ) can be deployed through catheter 710, thereby delivering the drug to the treatment site. In some cases, catheter 710 can be removed after drug solution 740 is delivered. When another treatment is needed, catheter 710 can be advanced over guide wire 730 into position, and another administration of drug solution 740 can be deployed.

Figure 7B:
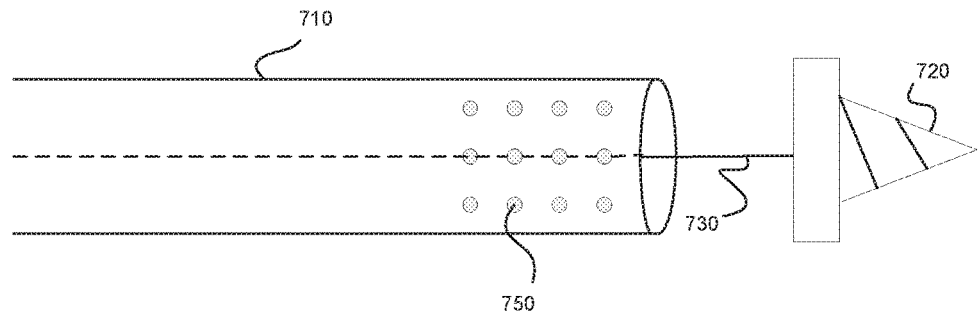

With reference to FIG. 7B, drug delivery device 701 can include a catheter or tubular member 710, an anchor 720, and a guide wire 730. In this case, catheter 710 can have a distal end region that includes multiple openings 750. Openings 750 can be smaller than the opening, if present, at the distal end of catheter 710 which allows for advancement over guide wire 730. In some cases, catheter 710 of device 701 can be configured to remain with the patient. When another treatment is needed, a drug or a drug solution (e.g., a drug/polymer combination) can be pumped through catheter 710 and allowed to exit out of openings 750.

Figure 7C:
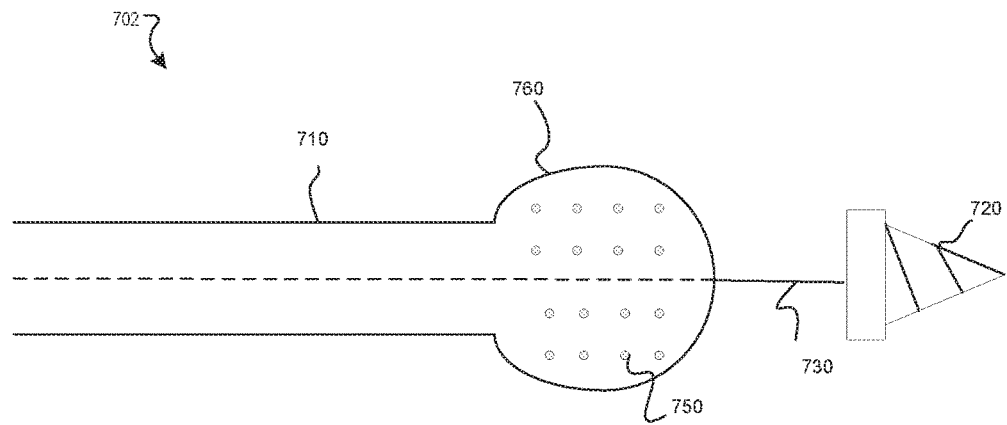

With reference to FIG. 7C, drug delivery device 702 can include a catheter or tubular member 710, an anchor 720, and a guide wire 730. In this case, catheter 710 can have a distal end region that includes balloon region 760. Balloon region 760 can include one or more openings 750 for allowing a drug or drug solution deployed through catheter 710 to exit catheter 710 and be delivered to a treatment site. In some cases, catheter 710 of device 702 can be configured to remain within the patient. When another treatment is needed, a drug or a drug solution (e.g., a drug/polymer combination) can be pumped through catheter 710 and allowed to exit out of openings 750.

Figure 7D:
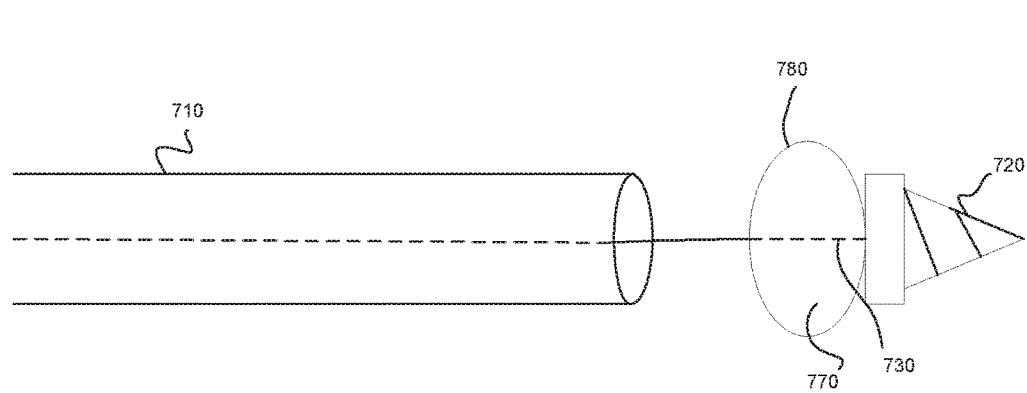

With reference to FIG. 7D, drug delivery device 703 can include a catheter or tubular member 710, an anchor 720, a guide wire 730, and a drug depot 770. Drug depot 770 can be configured to have a drug coating 780 and/or can be configured to elute a drug. In some cases, drug depot 780 can be configured as a refillable balloon structure. In such cases, catheter 710 can have a distal end region having the ability to engage drug depot 770 such that drug can be advanced along catheter 710 into drug depot 770. Drug depot 770 can be porous to allow a drug or drug solution to exit drug depot 770. In some cases, drug depot 770 can be configured to attach to anchor 720. In some cases, anchor 720, guide wire 730, and drug depot 770 can remain in the patient, while catheter 710 can be removed and reinserted when it is time to refill drug depot 770.

Figure 8:
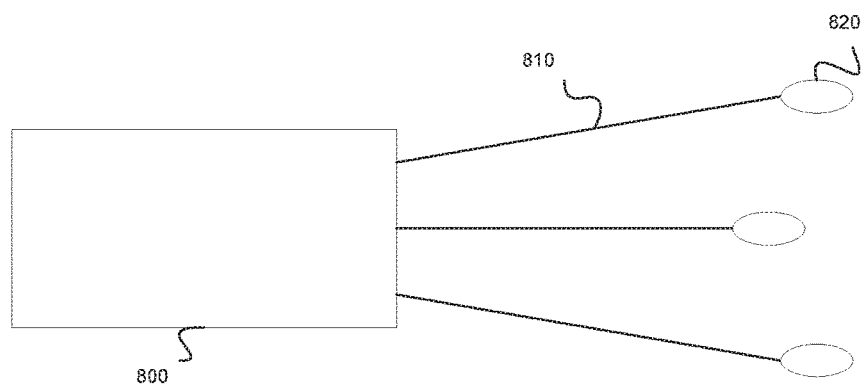
FIG. 8 is a side view of an exemplary system for providing a drug to multiple treatment sites.

In some cases, a device provided herein can include a pump configured to deliver drug (e.g., a drug solution, a drug eluting implant, and/or a suspension of controlled release particles containing one or more drugs). A pump provided herein can be positioned locally (e.g., at or near the treatment site) or remotely within the patient. In some cases, a pump provided herein can include control elements such that the pump can be actuated remotely (e.g., via radio frequencies). In some cases, a pump can include sensors designed to detect drug concentrations or the concentration of any other molecules suspected to be within the patient (e.g., cytokines such as TNF-α or interleukins). With reference to FIG. 8, one or more devices provided herein can be connected to pump 800. For example, pump 800 can be connected to a catheter, a guide wire, a pusher, or a combination thereof (as represented by figure numeral 810) such that drug can be delivered to the components at the treatment site (represented as figure numeral 820). In some cases, pump 800 can be connected to multiple devices to provide pumping action to different treatment sites.

Figure 9:
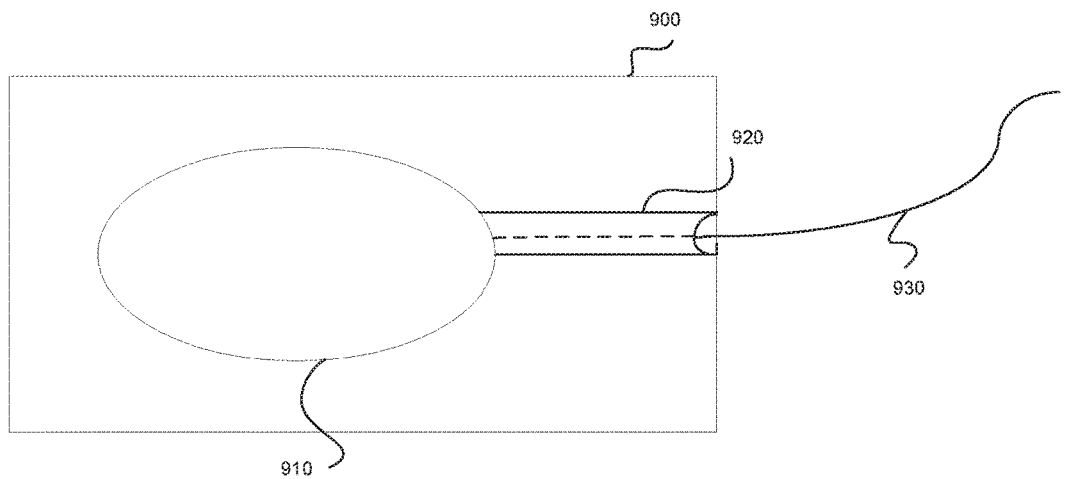
FIG. 9 is a side view of an exemplary system for providing a drug to a bone structure.

This document also provides implantable devices for performing a kyphoplasty procedure. For example, with reference to FIG. 9, a housing 910 can be implanted into a vertebral body 900. Housing 910 can be an inflatable balloon structure. In some cases, a bone port 920 can be attached to housing 910. Bone port 920 can be rigid and positioned to prevent bone from closing over guide wire 930. Housing 910 can contain a drug to be delivered to the site of the vertebral body. In some cases, housing 910 can contain a drug and a bone cement material (e.g., PMMA). When additional drug or other materials are to be delivered to housing 910, a catheter can be advanced over guide wire 930 and can attach to bone port 920 or housing 910. At this point, the drug or other materials can be delivered to housing 910 via the catheter.

Figure 10A:
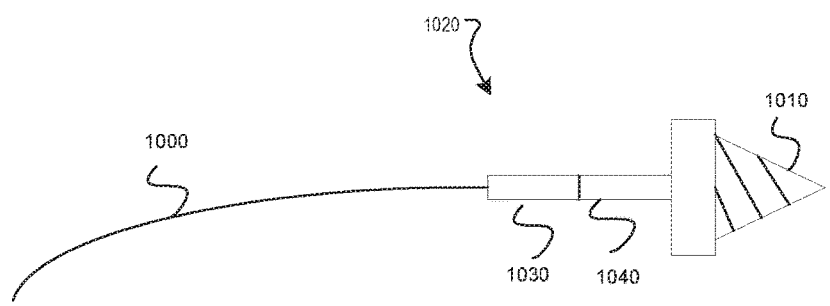
FIGS. 10A-B are side views of exemplary guide wire configurations.
Figure 10B:
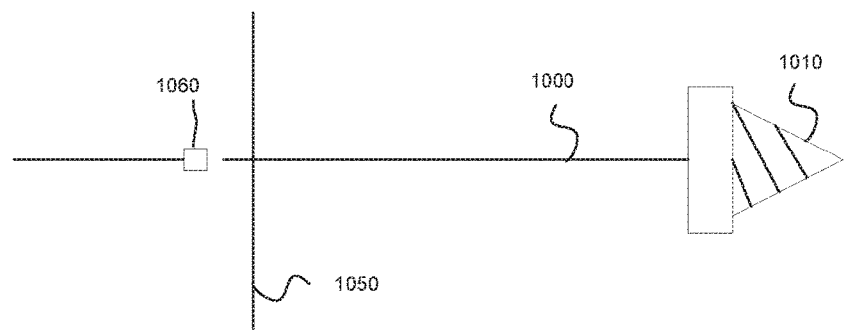

In some cases, a guide wire of a device provided herein can be detachable from and re-attachable to the component that is configured to attach to. For example, a guide wire can be configured to releasably attach to an anchor. In some cases, a portion of a guide wire can be detachable from and re-attachable to another portion of the guide wire. The releasably attached guide wire or portion of a guide wire can be released by a pull-apart mechanism, a lock/unlock mechanism, or a twist on/twist off mechanism. In some case, a coupling can be used to releasably attach a guide wire or portion of a guide wire. With reference to FIG. 10A, a guide wire 1000 can be connected to anchor 1010 via a coupling 1020. Coupling 1020 can include a first member 1030 (e.g., a male connector) fixedly attached to guide wire 1000 and a second member 1040 (e.g., a female connector) fixedly attached to anchor 1010. First member 1030 and second member 1040 can mate to form the releasable connection between guide wire 1000 and anchor 1010. With reference to FIG. 10B, a guide wire 1000 can extend from an anchor 1010 that is positioned into a treatment site within a mammal to the surface of the mammal's skin 1050. A coupler 1060 can allow another portion of guide wire 1000 to be removed or attached to the portion within the mammal. In some cases, excess guide wire can be tucked under the mammal's skin. Coupler 1060 can be any type of connection including a snap coupler, a screw-type coupler, or a hook/eyelet coupler. In some cases, a spooling device can be used to hold excess guide wire. A spooling device can be a manual feed spooling device or an automatically winding spooling device. Such a spooling device can be reusable or disposable. In some cases, a spooling device can hold excess guide wire that extends past the surface of the patient's skin. In such cases, the spooling device can house the excess guide wire and can be implanted under the patient's skin in a small subcutaneously created pocket that approximates the size of the spooling device. For example, a spooling device can be a silicon, titanium, or silastic spooling device that can be tucked under the patient's skin into a pocket. In some cases, an automated spooling device that functions in a manner similar to that of a standard tape measure can be used. For example, an automated spooling device can be configured to automatically reel wire (e.g., excess wire into or around a housing upon activation of a button or lever). FIGS. 13-20 contain photographs of exemplary spooling devices that can be used as described herein. In some cases, a spooling device can be configured to be no bigger than a quarter (e.g., about the size of a quarter, less than the size of a quarter, about the size of a nickel, less than the size of a nickel, about the size of a penny, less than the size of a penny, about the size of a dime, or less than the size of a dime).

Figure 11A:
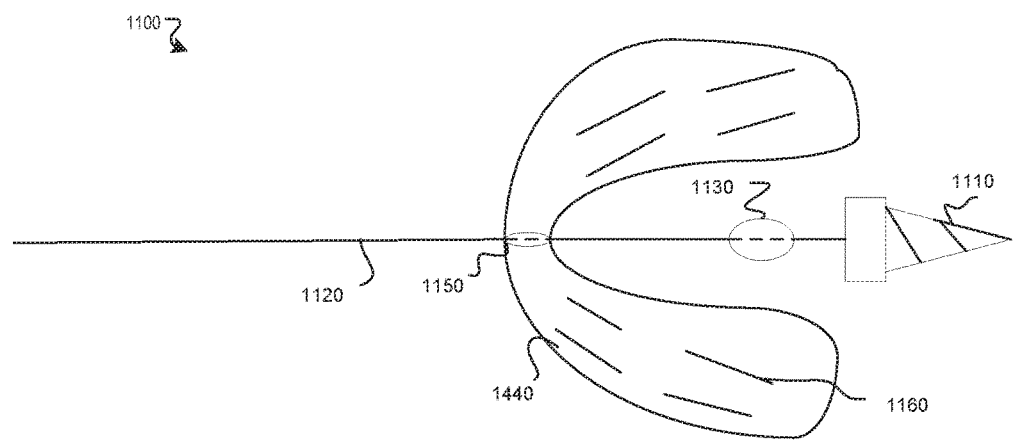
FIGS. 11A-B are side views of exemplary systems for delivering electrical stimulation to a treatment site.

This document also provides implantable electrode devices containing electrodes configured to stimulate tissue. For example, a device provided herein can be configured to include one or more electrodes. In some cases, an electrode device can be advanced over a guide wire of a device provided herein. An electrode device provided herein can be used to provide electrical stimulation to a target tissue such as a spinal nerve dorsal root ganglia, lumbar/sacral plexus nerves, or facet or sacroiliac joints. With reference to FIG. 11A, system 1100 can include an anchor 1110 and a guide wire 1120. A drug eluting implant 1130 can be advanced along guide wire 1120 as described herein. In some cases, an electrode device 1140 can be advanced along guide wire 1120 such that it can be positioned at a treatment site. Electrode device 1140 can be expandable such that it can be deployed in a compact configuration and be expanded once at the treatment site. Electrode device 1140 can have any appropriate shape including, without limitation, balloon shapes, bulb shapes, leaflet shapes, and fan shapes. In some cases, electrode device 1140 can include a structure 1150 (e.g., a ring or loop structure) to allow electrode device 1140 to be advanced along guide wire 1120. In some cases, electrode device 1140 can be configured to include multiple electrodes 1160. Electrical current can be provided to electrodes 1160 via guide wire 1120.

Figure 11B:
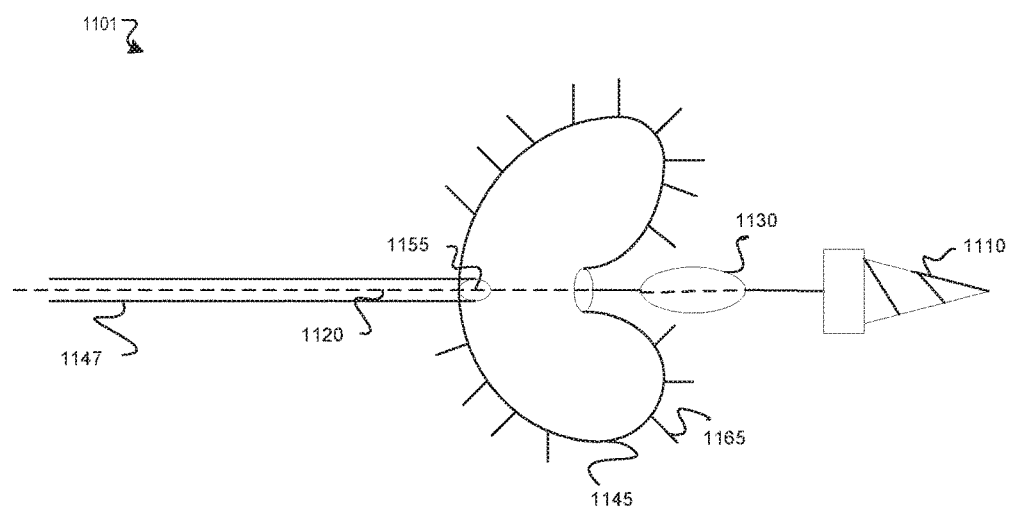

With reference to FIG. 11B, system 1101 can include an anchor 1110 and a guide wire 1120. A drug eluting implant 1130 can be advanced along guide wire 1120 as described herein. In some cases, an electrode device 1145 can be advanced along guide wire 1120 such that it can be positioned at a treatment site. Electrode device 1145 can be expandable such that it can be deployed in a compact configuration and be expanded once at the treatment site. Electrode device 1145 can have any appropriate shape including, without limitation, balloon shapes, bulb shapes, leaflet shapes, and fan shapes. In some cases, electrode device 1145 can be permanently or releasably attached to an inflation/deflation catheter 1147. Inflation/deflation catheter 1147 can be configured to allow electrode device 1145 to be inflated or deflated. In some cases, inflation/deflation catheter 1147 can be releasably connected to electrode device 1145 via connection 1155. Electrode device 1145 can be configured to include multiple electrodes 1165. Electrical current can be provided to electrodes 1165 via guide wire 1120 and/or inflation/deflation catheter 1147.

Figure 5E:
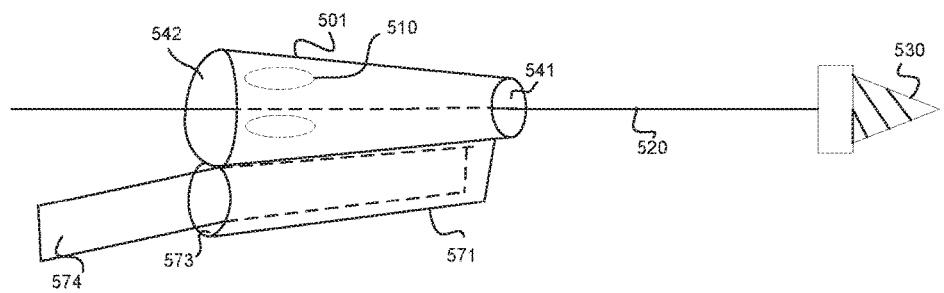

In some cases, a carrier can be used to deliver and/or hold an electrode body. For example, with reference to FIG. 5E, carrier 501 can be configured to entirely or at least partially house one or more drug eluting implants 510. Carrier 501 can be configured to deliver drug eluting implant 510 along guide wire 520 toward anchor 530. In some cases, carrier 501 can be configured to have a small open end 541 and a large open end 542. These open ends can allow carrier 501 to be advanced along guide wire 520 toward anchor 530. In some cases, carrier 501 can include an electrode device compartment 571. Electrode device compartment 571 can be configured to entirely or at least partially house one or more electrode bodies 574 within opening 573. Opening 573 and electrode device compartment 571 can be configured to hold an inserted electrode body in a manner that prevents excessive movement of the inserted electrode body.

Figure 5F:
Figure 5F:
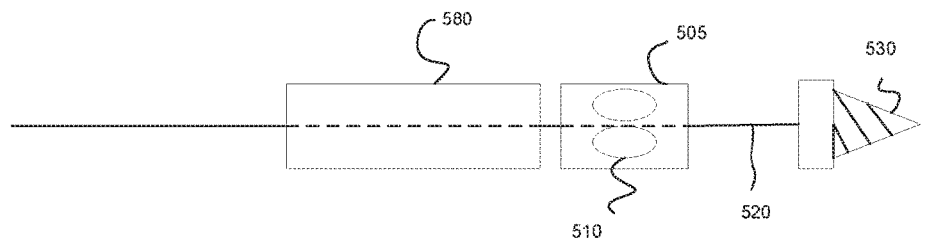

Referring now to FIG. 5F, a system 575 can include a guide wire 520 and an anchor 530. A carrier 505 can be configured to advance along guide wire 520 to be positioned at a treatment site. Carrier 505 can be configured to house, entirely or at least partially, one or more drug eluting implants 510. In some cases, system 575 can include a second carrier 580. Carrier 580 can be configured to entirely or at least partially house one or more electrode bodies (not shown). In some cases, a distal end surface of second carrier 580 can be configured to releasably attach to a proximal end surface of carrier 505. For example, a snap fit, a screw connection, or a magnetic mechanism can be used to attach a distal end surface of second carrier 580 to a proximal end surface of carrier 505.

Figure 6F:
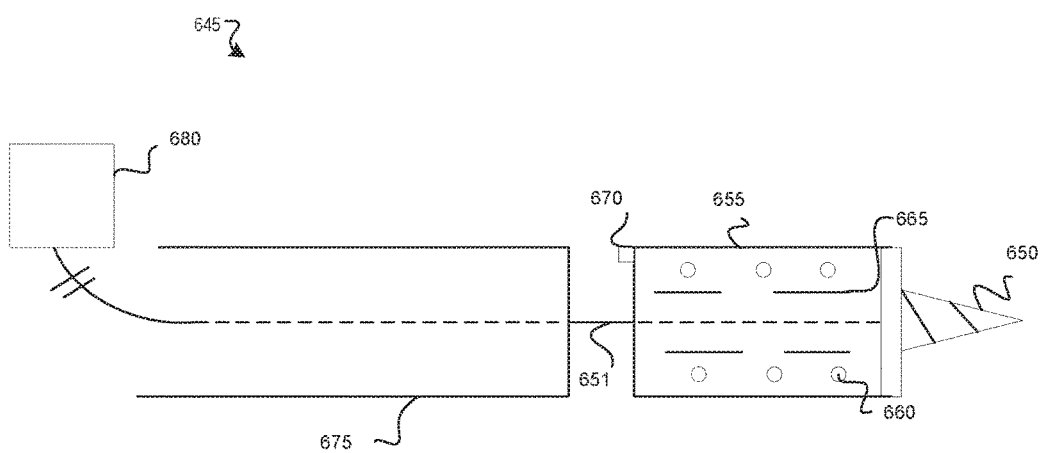

Referring now to FIG. 6F, a system 645 can include an anchor 650 and a guide wire 651. A drug eluting reservoir device 655 can be configured to advance along guide wire 651 to be positioned at a treatment site. In some case, drug eluting reservoir device 655 can be permanently or releasably attached to anchor 650. In some cases, drug eluting reservoir device 655 can be configured to having openings 660. Openings 660 can allow a drug housed within drug eluting reservoir device 655 to be released to the treatment site. Drug eluting reservoir device 655 can include a port 670 (e.g., a septum) to allow additional drug to be delivered into drug eluting reservoir device 655. For example, drug eluting reservoir device 655 can be refilled with drug via port 670. In some cases, drug eluting reservoir device 655 can be configured to having one or more electrodes 665. Electrodes 665 can be configured to provide electrical stimulation to a treatment site. In some cases, system 645 can include an insulating catheter 675. Insulating catheter 675 can provide appropriate insulation to electrical connections attached to electrodes 665. In some cases, guide wire 651 can be used to supply current to electrodes 665. In such cases, guide wire 651 can be attached to a generator 680. Any appropriate type of generator can be used to supply current to the electrodes of a device provided herein. For example, radiofrequency coupled devices or rechargeable/non-rechargeable internal pulse generators can be used to supply current to the electrodes of a device provided herein. In some cases, a device having an electrode can be configured to include a microgenerator. For example, a microgenerator can be configured to be part of the same device that contains electrodes. Examples of microgenerators that can be used as described herein include, without limitation, those described in U.S. Pat. No. 6,061,596, U.S. Pat. No. 6,181,965, or Published PCT Application No. WO 97/29802. In some cases, insulating catheter 675 can include a lumen for delivering fluid to drug eluting reservoir device 655. Such a lumen can attach to port 670.

This document also provides implantable bioport devices. For example, this document provides bioport devices that can be attached to an anchor (e.g., a tissue anchor) and can be configured to elute one or more drugs to a treatment location. In some cases, an implantable bioport device provided herein can include monitoring electronics to detect the local concentrations of molecules such as the delivered drug(s) or polypeptides produced by the mammal being treated (e.g., inflammatory cytokines such as TNF-$\alpha$, IL-6, IL-8, IL-11$\beta$, or matrix metalloproteinases).

In some cases, an implantable bioport device can be anchored to tissue such as a vertebral body, pedicle, transverse process, facet, or sacroiliac joint in a similar manner as described herein with respect to a guide wire. A bioport device can be refilled from a percutaneous approach with various medications to treat, e.g., pain emanating from these structures. In some cases, a bioport device can fit onto an anchor screw so as to allow rigidity or can be attached such that it would hang at an angle to the anchor to allow it to more closely approximate the distance to the target tissue. The bioport device can be filled with small beads, crystals, or fluid that can be slowly released to the area of the target tissues. In some cases, a bioport device can be cannulated from a percutaneous approach to allow the continuous infusion of medications to the target tissues.

Figure 3:
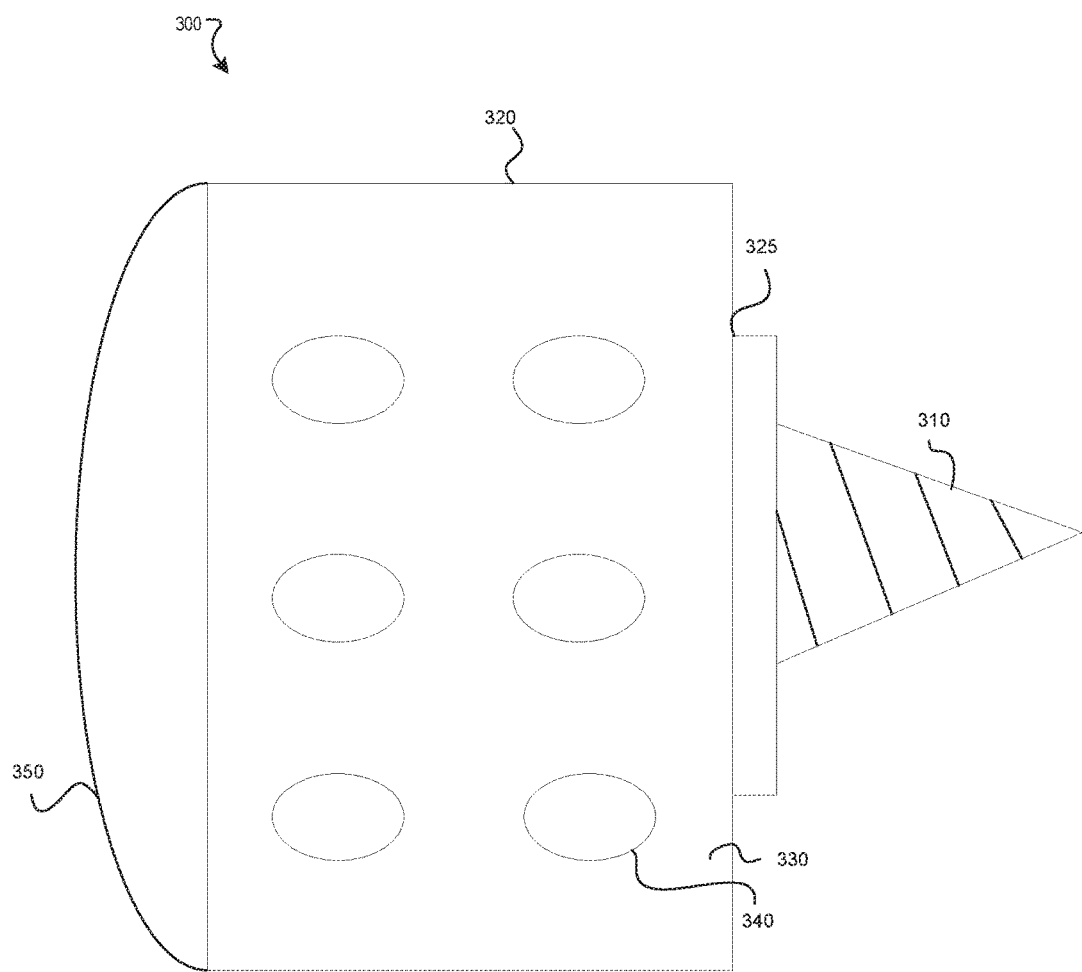
FIG. 3 is a side view of an example of a device for delivering a drug to a treatment site.

With reference to FIG. 3, system 300 can include an anchor 310 and an implantable bioport device 320. Anchor 310 can be inserted into any type of tissue. For example, anchor 310 can be inserted into bone, such as a posterior aspect of a vertebral body near an exiting spinal nerve. In some cases, anchor 310 can be a bone screw, a nitinol corkscrew anchor, or other bone/tissue anchoring device. Implantable bioport device 320 can be configured to house one or more drug eluting pod implants such as those described herein. In some cases, implantable bioport device 320 can house monitoring electronics configured to detect the local concentrations of molecules such as a delivered drug or polypeptide produced by the mammal. Implantable bioport device 320 can be integral with or releasably attached to anchor 310. For example, implantable bioport device 320 can be configured to releasably attach to anchor 310 via a snap fitting or thread connection 325. A surface of implantable bioport device 320 (e.g., side wall 330) can be configured to have one or more openings 340. The drug of a drug eluting pod implant located within implantable bioport device 320 can be released from implantable bioport device 320 via openings 340. In some cases, implantable bioport device 320 can include a membrane structure 350. Membrane structure 350 can be configured to allow a needle to access the interior of implantable bioport device 320. In some cases, membrane structure 350 can be dome-shaped. During use, system 300 can be implanted into a patient such that anchor 310 and implantable bioport device 320 remain within the patient without a guide wire or catheter.

Figure 21:
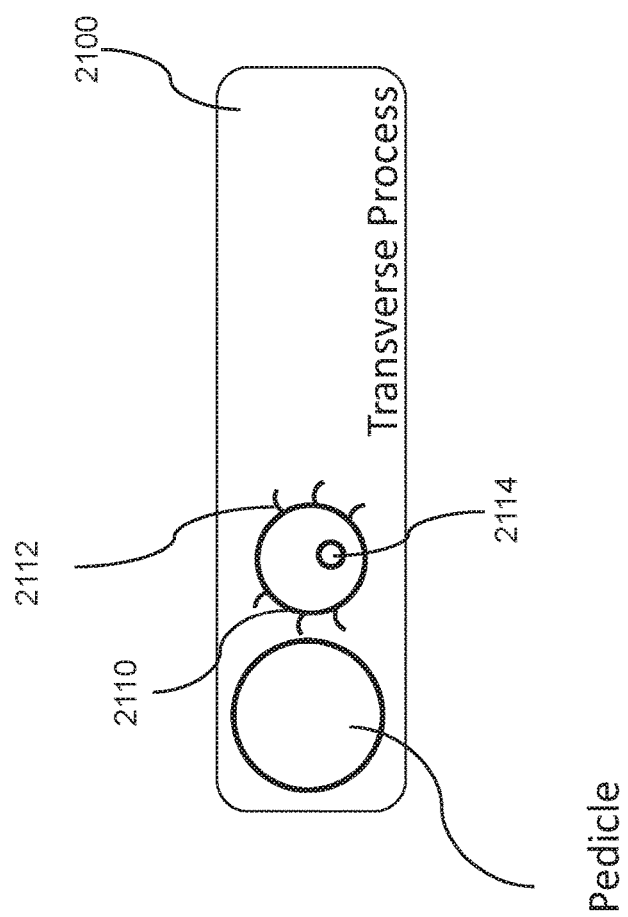
FIG. 21 is a side view of an example of a device for delivering a drug to a transverse process of a vertebra.

With reference to FIG. 21, a bioport 2110 can include a body section and one or more anchors 2112 (e.g., screws or prong-like anchors). The bioport can be anchored to any appropriate tissue as described herein. In some cases when treating, for example, facet joint pain, a bioport can be anchored to a transverse process. For example, as shown in FIG. 21, bioport 2110 can be anchored to transverse process 2100 via anchors 2112. Bioport 2110 can be filled with a drug or agent to be delivered such as an anesthetic or corticosteroid. In some cases, the bioport can be filled with small beads, crystals, or fluids that can be slowly released to the area of the target tissues. When using drugs or agents in liquid form, the bioport can be constructed of material that allows the liquid drugs or agents to be released slowly over a desired time frame (e.g., over a week, a month, or a two month time frame). When using drugs or agents in solid form (e.g., a time release formulation or a drug eluting implant provided herein), the bioport can be constructed of material that allows emitted drugs or agents to exit the bioport freely. For example, the bioport can be constructed of porous or mesh-like material. In some cases, bioport 2110 can include a fill port 2114. Fill port 2114 can be used to insert additional material into the bioport. For example, fill port 2114 can be used to refilled the bioport from a percutaneous approach with various medications to treat, e.g., facet joint pain. In some cases, fill port 2114 can include material to aid in locating its position within a body. For example, fill port 2114 can include material that aids in locating the fill port by X-ray or ultra sound.

In some cases, fill port 2114 can be a self-sealing port such that a needle can be repeatedly inserted and withdrawn without leaving an opening in the port when withdrawn. In some cases, the fill port 2114 can be used as a docking port such that a cannula or tube structure can engage the bioport. Such a cannula or tube structure can be used to deliver material (e.g., drugs or agents) to the bioport. In some cases, the cannula or tube structure can include the ability to deliver electrical current to the bioport, and the bioport can include one or more electrode configured to deliver electrical stimulation to target tissue. In some cases, a bioport can be configured to deliver radio frequencies such that radio frequency ablation can be performed on desired tissue (e.g., nerve tissue for a facet joint pain treatment).

Figure 22A:
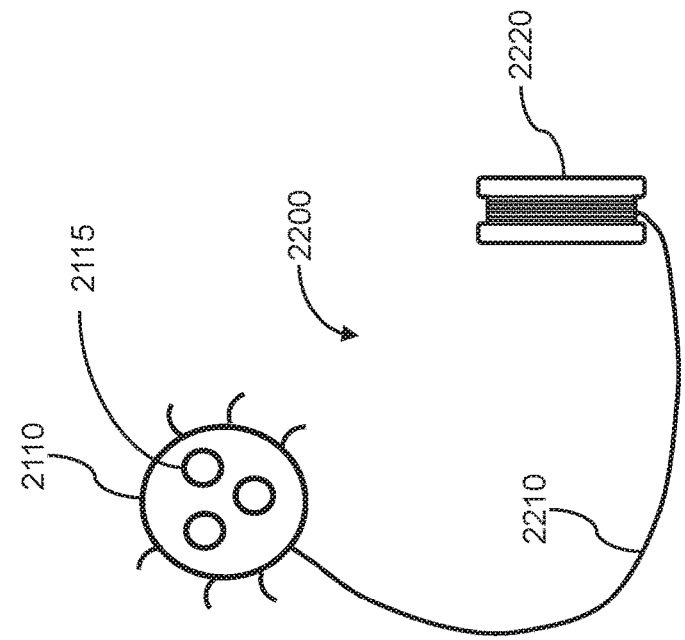
FIG. 22A is a view of an example of a device for delivering a drug to a treatment site with the spooling device shown from the side.
Figure 22B:
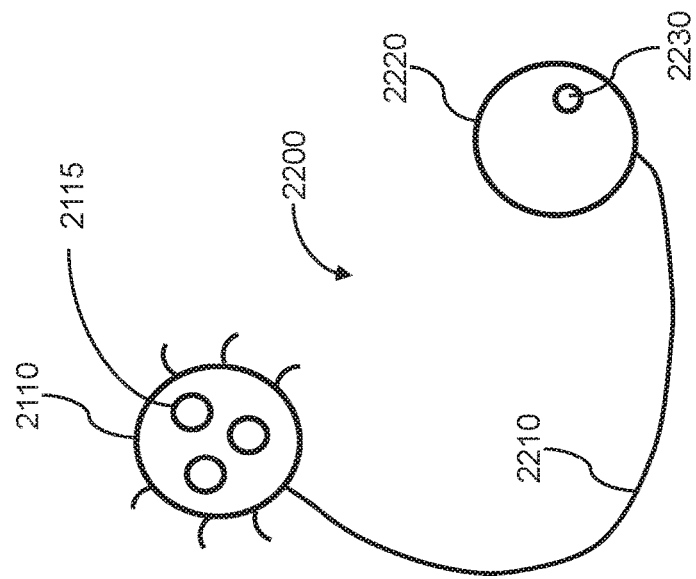
FIG. 22B is a view of the device from FIG. 22A with the spooling device shown from the top.

During use, bioport 2110 can be implanted into a patient such that bioport 2110 remains within the patient with a guide wire or catheter. In some cases, bioport 2110 can be connected to a wire-like structure 2210 (e.g., a wire with or without a lumen) as shown in FIGS. 22A and 22B. In some cases, wire-like structure 2210 can be directly attached to a spooling device 2220. Spooling device 2220 can house any excess wire length when the bioport is implanted in a patient. In some cases, a wire-like structure 2210 having a lumen can be connected to a spooling device having a fill port 2230. Fill port 2230 can allow materials to be inserted into the spooling device and advanced along the inner lumen of the wire-like structure for delivery to the bioport. Such materials can be in liquid or solid form. When in solid form, a pusher can be used to advance the material along the inner lumen of the wire-like structure for delivery to the bioport. In some cases, material can be inserted directly into the lumen of wire-like structure 2210 to be delivered to the bioport. In some cases, wire-like structure 2210 can be insulated to provide electrical current to the bioport for use in providing electrical stimulation. In some cases, bioport 2110 can include one or more elution ports 2115 configured to allow sustained release of drugs or agents from the bioport.

Figure 23B:
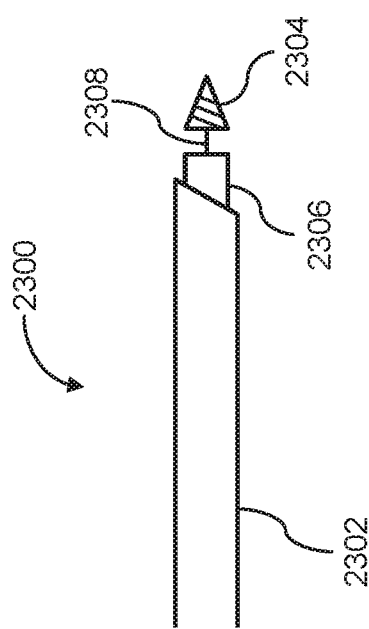
FIG. 23B is a view of the device from FIG. 23A following deployment from a delivery catheter (e.g., a needle).
Figure 23A:
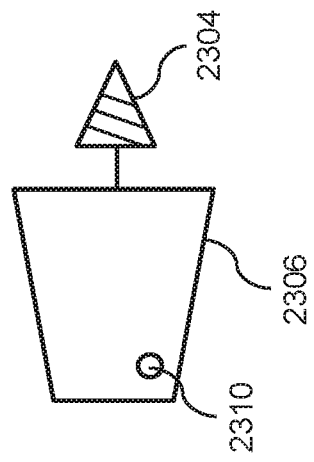
FIG. 23A is a view of an example of a device for delivering a drug to a treatment site.

During use, a bioport can be implanted into a patient such that the bioport remains within the patient without a guide wire or catheter. In some cases, a bioport can be delivered using a cannula (e.g., a 12 gauge needle). In such cases, the bioport can be an expandable device (e.g., a device made of shape memory material or a balloon) that is in a compressed configuration during delivery while within the cannula. Once deployed outside the cannula, the compressed bioport can expand. With reference to FIGS. 23A and 23B, system 2300 can include cannula 2302 for delivering bioport 2306. Bioport 2306 can include an anchor 2304. Anchor 2304 can be indirectly attached to a body portion of bioport 2306 via a tethering portion 2308. In some cases, anchor 2304 can be directly attached to a body portion of bioport 2306. When located within cannula 2302, a body portion of bioport 2306 can be in a compressed configuration as shown in FIG. 23A. Once deployed, a body portion of bioport 2306 can expand as shown in FIG. 23B. Bioport 2306 can include a fill port 2310. Fill port 2310 can be similar to fill port 2114, and bioport 2306 can be similar to bioport 2110.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A method for percutaneously delivering a drug to a mammal, wherein said method comprises:
 (a) advancing a guide wire having a distal end and a proximal end into a position within said mammal such that the distal end of said guide wire is located at or near a site to be treated, wherein said distal end of said guide wire comprises a tissue anchor device, wherein said tissue anchor device is releasably attached to said distal end of said guide wire by means of a lock/unlock mechanism,
 (b) attaching said tissue anchor device to a tissue located at or near said site,
 (c) positioning a drug eluting implant along said guide wire at a position located at or near said site,

(d) positioning said proximal end of said guide wire at or near the surface of the skin of said mammal, and (e) leaving said guide wire in said position for at least five days.

2. The method of claim 1, wherein said mammal is a human.

3. The method of claim 1, wherein said guide wire is constructed of nitinol.

4. The method of claim 1, wherein said guide wire is configured to have a length such that said distal end of said guide wire is located within 1 cm of said site to be treated and said proximal end of said guide wire is located within 1 cm of said surface of the skin of said mammal.

5. The method of claim 1, wherein said drug eluting implant is a clonidine eluting implant.

6. The method of claim 1, wherein said drug eluting implant is bioabsorbable.

7. A method for percutaneously delivering a drug to a mammal, wherein said method comprises:

(a) advancing a guide wire having a distal end and a proximal end into a position within said mammal such that the distal end of said guide wire is located at or near a site to be treated, wherein said distal end of said guide wire comprises a tissue anchor device, wherein said tissue anchor device is releasably attached to said distal end of said guide wire by means of a twist on/twist off mechanism, (b) attaching said tissue anchor device to a tissue located at or near said site, (c) positioning a drug eluting implant along said guide wire at a position located at or near said site, (d) positioning said proximal end of said guide wire at or near the surface of the skin of said mammal, and (e) leaving said guide wire in said position for at least five days.

8. The method of claim 7, wherein said mammal is a human.

9. The method of claim 7, wherein said guide wire is constructed of nitinol.

10. The method of claim 7, wherein said guide wire is configured to have a length such that said distal end of said guide wire is located within 1 cm of said site to be treated and said proximal end of said guide wire is located within 1 cm of said surface of the skin of said mammal.

11. The method of claim 7, wherein said drug eluting implant is a clonidine eluting implant.

12. The method of claim 7, wherein said drug eluting implant is bioabsorbable.

13. A method for percutaneously delivering a drug to a mammal, wherein said method comprises:

(a) advancing a guide wire having a distal end and a proximal end into a position within said mammal such that the distal end of said guide wire is located at or near a site to be treated, wherein said distal end of said guide wire comprises a tissue anchor device, wherein said tissue anchor device is releasably attached to said distal end of said guide wire by means of a coupling comprising a first member and a second member, wherein said first member comprises a male connector, and wherein said second member comprises a female connector, (b) attaching said tissue anchor device to a tissue located at or near said site, (c) positioning a drug eluting implant along said guide wire at a position located at or near said site, (d) positioning said proximal end of said guide wire at or near the surface of the skin of said mammal, and (e) leaving said guide wire in said position for at least five days.

14. The method of claim 13, wherein said mammal is a human.

15. The method of claim 13, wherein said guide wire is constructed of nitinol.

16. The method of claim 13, wherein said guide wire is configured to have a length such that said distal end of said guide wire is located within 1 cm of said site to be treated and said proximal end of said guide wire is located within 1 cm of said surface of the skin of said mammal.

17. The method of claim 13, wherein said drug eluting implant is a clonidine eluting implant.

18. The method of claim 13, wherein said drug eluting implant is bioabsorbable.

* * * * *